United States Patent
Zong et al.

(10) Patent No.: US 8,300,226 B2
(45) Date of Patent: Oct. 30, 2012

(54) METHOD FOR DETECTING SURFACE PLASMON RESONANCE

(75) Inventors: Yun Zong, Singapore (SG); Wolfgang Knoll, Singapore (SG); Xiaodi Su, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 240 days.

(21) Appl. No.: 12/312,715

(22) PCT Filed: Nov. 23, 2007

(86) PCT No.: PCT/SG2007/000404
§ 371 (c)(1),
(2), (4) Date: Feb. 4, 2010

(87) PCT Pub. No.: WO2008/063139
PCT Pub. Date: May 29, 2008

(65) Prior Publication Data
US 2010/0128272 A1    May 27, 2010

Related U.S. Application Data

(60) Provisional application No. 60/860,903, filed on Nov. 24, 2006.

(51) Int. Cl.
*G01N 21/55* (2006.01)
(52) U.S. Cl. .................................................. 356/445
(58) Field of Classification Search ........... 356/445–448
See application file for complete search history.

(56) References Cited

U.S. PATENT DOCUMENTS

| 6,161,437 A | 12/2000 | Brennan et al. |
| 6,567,753 B2 * | 5/2003 | Potyrailo .................... 702/39 |
| 2002/0173922 A1 * | 11/2002 | Potyrailo .................... 702/39 |

FOREIGN PATENT DOCUMENTS

| DE | 4 041 851 A1 | 7/1992 |
| WO | WO 2006/031198 A1 | 3/2006 |

OTHER PUBLICATIONS

Bailey, L., et al., "Using Surface Plasmon Resonance and the Quartz Crystal Microbalance to Monitor in Situ the Inerfacial Behavior of Thin Organic Films," *Langmuir* 18(2):479-489, American Cancer Society, United States (2002).

The Written Opinion of the International Searching Authority for International Patent Application No. PCT/SG2007/00404, Australian Patent Office, Australia, mailed on Feb. 8, 2008.

The International Preliminary Report on Patentability for International Patent Application No. PCT/SG2007/00404, Australian Patent Office, Australia, mailed on Sep. 24, 2008.

* cited by examiner

*Primary Examiner* — Michael P Stafira
(74) *Attorney, Agent, or Firm* — Sterne, Kessler, Goldstein & Fox P.L.L.C.

(57) ABSTRACT

There is disclosed a method and system for detecting a surface plasmon resonance associated with a fluid sample. The method includes the step of providing a piezoelectric substrate having at least two electrodes thereon, wherein at least one of said electrodes is coupled to a fluid sample. A light beam is transmitted toward the fluid sample to induce a oscillation frequency in the piezoelectric substrate. The oscillation frequency from said electrodes is then measured during transmittance of the light to detect the surface plasmon resonance associated with the fluid sample.

20 Claims, 11 Drawing Sheets

US 8,300,226 B2

METHOD FOR DETECTING SURFACE PLASMON RESONANCE

TECHNICAL FIELD

The present invention generally relates to a surface plasmon resonance detection method and to a system for implementing the same. In one embodiment, both surface plasmon resonance and gravimetric detection is undertaken.

BACKGROUND

Surface Plasmon Resonance (SPR) and microgravimetric sensing techniques, such as Quartz Crystal Microbalance (QCM), are known independently as methods suitable for in-situ, label-free sensing and analysis of binding reactions. Sensors using SPR or QCM have been used to analyse biological, biochemical and chemical samples.

Conventional QCM devices comprise a quartz crystal wafer having two planar metal electrodes disposed on the two surfaces of the wafer. The sample to be analysed is adsorbed onto the surface of one of the electrodes. The change in the quartz crystal can be excited to mechanical resonance by an alternating electric field due to the inverse piezoelectric effect. The oscillation frequency is dependent upon the mass and the viscoelastic property of material adsorbed onto the surface electrode. In general, the oscillation frequency decreases if mass accumulates and increases if mass reduces. In some instances (for example, where the adsorbed layer is rigid), the shift in the oscillation frequency can be related to the adsorbed mass using analytical equations. A mass loading in the order of about 1 ng/cm$^2$ can be detected.

SPR is a known method for the detection of optical changes occurring at the surface of a thin metal film. SPR measures changes in the optical thickness (calculated by assuming a reasonable refractive index for the absorbed layer, may not be equal to the geometrical thickness) arising from molecular adsorption on the metal surface. In SPR, an evanescent wave (which is an exponential-decaying wave) presents at the sensor surface. An evanescent wave is generated when total internal reflection of incident light occurs at the interface of a substance with a high refractive index and a substance of low refractive index (e.g. a glass-air interface of a prism). SPR occurs under certain conditions when a thin film of metal (e.g. gold or silver) is placed on the bottom of a prism or one side of a planar substrate of the same material whose opposite side is attached to the bottom of the prism via a thin layer of an index-matched liquid. If the incident light is monochromatic, the free electrons of the metal will oscillate (i.e. surface Plasmon Polaritons are excited) and absorb light energy at a certain angle of incidence. The angle is called the SPR angle. The SPR signal is detected by measuring the intensity of the reflected light using a photodiode detector. With an appropriate metal thickness (~47 nm for gold and ~50 nm for silver) and a satisfied flatness (roughness less than a few nanometers), almost all light is coupled to excite Surface Plasmon Polaritons which "illuminate" at the surface and propagate along the surface at the resonance angle. As a consequence, the reflectivity drops to ~0.

The position of the SPR angle depends on the optical property changes of the sensing surface due to the binding of molecules to the surface or the removal of the materials from the surface. The shift of SPR angle can be correlated to the amount of molecules adsorbed/desorbed at the surface by assuming a reasonable refractive index. The detection limitation of SPR is approximately 1 ng/cm$^2$.

SPR and QCM techniques each have their own specific strengths, weaknesses and have assumptions that are inherent in data collection and analysis. Accordingly, each technique is sensitive to different properties of a thin film sample.

Analytical devices that combine both SPR and QCM techniques are known. These combinations, however, generate complexities which result in inaccurate or irreproducible experimental results. For example, when a piece of metal-electrode furnished quartz crystal wafer is placed in a QCM sample cell with a transparent sealing window (e.g., glass), interference of the reflected beams off the cell window and off the quartz crystal wafer surface adversely affects the intensity of the reflected light ultimately reaching the photodiode detector of the SPR analyzer. As a result, the SPR spectrum, i.e. a summary of the reflectivity data measured at each angle of incidence, would be based on the resultant superimposition of the unwanted reflected light off the cell window (glass) and the desired reflected light off the quartz crystal wafer surface, thereby roughening the spectrum and making accurate detection barely possible. Other stray light sources that would potentially interfere with the desired reflected light also pose a problem for these hybrid analytical systems.

Moreover, the setup of these hybrid analytic systems are fairly complicated and requires the presence of other components such as a lock-in amplifier, a photodiode detector, a detector motor, a frequency modulator (a light chopper) and a light polarizer(s) to be present. The need for the presence of a large amount of auxiliary components also portends a higher likelihood of achieving inaccurate results due to the increased number of additional parameters that have been introduced. Furthermore, the elaborate setup which follows when combining QCM and SPR makes it economically undesirable. This explains why the implementation of such hybrid systems is not common.

There is a need to provide a surface plasmon resonance sensing method that overcomes, or at least ameliorates, one or more of the disadvantages described above.

There is also a need to provide a method and system for combining surface plasmon resonance and gravimetric sensing, such as QCM, which avoids, or at least ameliorates, one or more of the disadvantages described above.

SUMMARY

According to a first aspect, there is provided a method for detecting surface plasmon resonance associated with a fluid sample, the method comprising the steps of:

providing a piezoelectric substrate having at least two electrodes thereon, wherein at least one of said electrodes is coupled to a fluid sample;

transmitting a light beam toward the fluid sample to induce an oscillation frequency in the piezoelectric substrate; and measuring the oscillation frequency from said electrodes during transmittance of said light to detect surface plasmon resonance associated with the fluid sample.

Advantageously, the surface plasmon resonance (SPR) measurement is determined from the electrodes coupled to the piezoelectric substrate. Advantageously, the method does not rely on reflected light to determine the SPR signals, thus eliminating the need for a photodiode and related auxiliary components from conventional SPR equipment, such as lock-in amplifiers and choppers. More advantageously, the method does not need to filter off the s-polarized light (if any), thereby eliminating polarizers from conventional SPR equipment.

In one embodiment, there is provided a method according to the first aspect further comprising the step of using the measured oscillation frequency to determine a gravimetric measurement of the fluid sample.

Advantageously, the disclosed method may aid in the generation of a single experimental platform (such as a piece of grating-featured piezoelectric substrate) that may be used as a basis for both a surface plasmon resonance measurement and a gravimetric measurement of the same binding reaction at substantially the same surface.

In one embodiment, the surface plasmon resonance measurement and the gravimetric measurement may be obtained in a continuous tandem manner. In another embodiment, the surface plasmon resonance measurement may be obtained at substantially the same time as the gravimetric measurement.

Advantageously, the disclosed method may substantially eliminate the need for more than one measurement device, one of which is used conventionally to measure a surface plasmon resonance signal and the other is used to measure a gravimetric signal independently of the first measurement device.

Advantageously, the inventors have found that by transmitting a light beam onto a piezoelectric substrate, the oscillation frequency of the piezoelectric substrate can be manipulated by changing the conditions of the light beam transmitted thereon.

In one embodiment, there is provided a method for detecting surface plasmon resonance and a gravimetric parameter associated with a fluid sample, the method comprising the steps of:

providing a piezoelectric substrate having at least two electrodes thereon, wherein at least one of said electrodes is coupled to a fluid sample; transmitting a light beam toward the fluid sample coupled to said piezoelectric substrate to induce an oscillation frequency in the piezoelectric substrate; and measuring the oscillation frequency from said electrodes during transmittance of said light to detect surface plasmon resonance and the gravimetric parameter associated with the fluid sample.

In another embodiment, there is provided a method for detecting surface plasmon resonance associated with a fluid sample, the method comprising the steps of:

providing a piezoelectric substrate having at least two electrodes thereon, wherein at least one of said electrodes is coupled to a fluid sample;

transmitting a light beam toward the fluid sample to induce an oscillation frequency in the piezoelectric substrate; and measuring the oscillation frequency from said electrodes during transmittance of said light to detect surface plasmon resonance associated with the fluid sample, with the proviso that reflected light from said transmitted light beam is not detected.

According to a second aspect, there is provided a system for detecting surface plasmon resonance associated with a fluid sample, the system comprising:

a piezoelectric substrate having at least two electrodes disposed thereon;

an enclosed chamber for retaining a fluid sample therein, wherein said enclosed chamber is arranged such that at least one of the electrodes is coupled to said fluid sample in use;

a light beam source arranged to transmit a light beam toward said fluid sample for inducing an oscillation frequency on said piezoelectric substrate; and a means for measuring the oscillation frequency from said electrodes during transmittance of said light to detect surface plasmon resonance associated with said fluid sample.

Advantageously, the disclosed system does not require the use of at least one component selected from the group consisting of a lock-in amplifier, a photodiode detector, a detector motor, a frequency modulator (a light chopper) and a light polarizer(s).

In one embodiment, there is provided a system for detecting surface plasmon resonance associated with a fluid sample, the system consisting essentially a piezoelectric substrate having at least two electrodes disposed thereon;

an enclosed chamber for retaining a fluid sample therein, wherein said enclosed chamber is arranged such that at least one of the electrodes is coupled to said fluid sample in use;

a light beam source arranged to transmit a light beam toward said fluid sample; and means for measuring the oscillation frequency from said electrodes during transmittance of said light to detect surface plasmon resonance associated with the fluid sample.

In another embodiment, there is provided a system for detecting surface plasmon resonance associated with a fluid sample, the system comprising:

a piezoelectric substrate having at least two electrodes disposed thereon;

an enclosed chamber for retaining a fluid sample therein, wherein said enclosed chamber is arranged such an enclosed chamber for retaining a fluid sample therein, wherein said enclosed chamber is arranged such that at least one of the electrodes is coupled to said fluid sample in use;

a light beam source arranged to transmit a light beam toward said sample; and means for measuring the oscillation frequency from said electrodes during transmittance of said light to detect surface plasmon resonance associated with the fluid sample with the proviso that reflected light from said transmitted light beam is not detected.

According to a third aspect there is provided the use of a system comprising: a piezoelectric substrate having at least two electrodes disposed thereon;

an enclosed chamber for retaining a fluid sample therein, wherein said enclosed chamber is arranged such that at least one: of the electrodes is coupled to said fluid sample in use;

a light beam source arranged to transmit a light beam toward said sample for inducing an oscillation frequency on said piezoelectric substrate; and means for measuring the oscillation frequency from said electrodes during transmittance of said light;

wherein said system is used to detect surface plasmon resonance associated with said fluid sample based on said measured oscillation frequency.

According to a fourth aspect there is provided a system for detecting light intensity comprising;

a piezoelectric substrate having at least two electrodes disposed thereon; a light beam source arranged to transmit a light beam toward said electrode on said piezoelectric substrate for inducing an oscillation frequency thereon; and means for measuring the oscillation frequency from said electrodes during transmittance of said light to determine the light intensity of said light beam source.

According to a fifth aspect, there is provided the use of a system comprising:

a piezoelectric substrate having at least two electrodes disposed thereon;

a light beam source arranged to transmit a light beam toward said piezoelectric substrate for inducing an oscillation frequency thereon; and means for measuring the oscillation frequency from said electrodes during transmittance of said light;

to determine the light intensity of said light beam source.

DEFINITIONS

The following words and terms used herein shall have the meaning indicated:

The term "fluid sample" is to be interpreted broadly to include any fluid material or mixture of fluid materials that contains one or more components of interest for a surface plasmon resonance analysis and, in some embodiments, surface plasmon resonance analysis and gravimetric analysis. The fluid material or mixture of fluid materials can either be in a liquid phase or a gaseous phase. The fluid sample may be a biological sample, a biochemical sample or a chemical sample. The fluid sample may be undergoing a reaction during the detection process. The reaction may include rigid or viscoelastic layer film formation, film layer removal, affinity binding, ligand-receptor binding, competitive binding and chemical reaction. Exemplary chemical reactions occurring in the fluid sample which may be measured include coupling of amino group functionalized molecules, macromolecules or particles to a carboxylic group terminated surface via an active ester intermediate (EDC/NHS coupling for aqueous condition and DCC/NHS coupling for non-aqueous condition), esterification polymerization and photo-polymerization of the components within said fluid sample.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise"; and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure of Optional Embodiments

Exemplary, non-limiting embodiments of a method for detecting surface plasmon resonance associated with a fluid sample will now be disclosed. The method comprises the step of providing a piezoelectric substrate having at least two electrodes thereon, wherein at least one of the electrodes is coupled to a fluid sample. One of the electrodes may be termed as the "front electrode". The front electrode may be furnished with a periodic metal surface corrugation (grating) structure. A light beam is transmitted toward the fluid sample that may be residing on the front electrode of the said piezoelectric substrate to induce a oscillation frequency detune in the piezoelectric substrate. The oscillation frequency from said electrodes is then measured during illumination of the light when the angle of incidence varies to detect the surface plasmon resonance associated with the fluid sample. In one embodiment, the fluid sample may reside on the electrode or the piezoelectric substrate or both.

Surface plasmon resonance (SPR) measurement refer to the measurement of a resonance condition that occurs when the tangential component of the wave vector of a light incident on the electrodes of the piezoelectric substrate matches the wave vector of the surface plasmons. At this condition, energy is transferred from the incident light to the surface plasmons. crystal microbalance measurement, surface acoustic wave measurement and bulk acoustic wave measurement.

Quartz crystal microbalance (QCM) measurement refers to a gravimetric measurement of a fluid sample when placed on a quartz crystal. When the fluid sample is placed onto or removed from the surface of the quartz crystal microbalance, the oscillation frequency of the quartz crystal microbalance will change accordingly. This frequency change depends on the mass of the fluid sample on the surface and the viscoelastic properties of the fluid sample. For formation of a rigid layer, the relationship between mass and change in frequency is shown by the Sauerbrey equation:

$$m_f = \frac{-\Delta f}{2f_q^2} \rho_q v_q$$

where $m_f$ is the mass density of the fluid sample adsorbed on the surface of the quartz crystal (kg/m$^2$), $\Delta f$ is the frequency change of the quartz crystal (Hz), $f_q$ is the initial frequency of the quartz, $\rho_q$ is the density of the quartz crystal (2650 kg/m$^3$) and $v_q$ is the shear wave velocity within the quartz (3340 m/s for an AT-cut crystal).

In one embodiment, the surface plasmon resonance (SPR) couples different amounts of light energy at different angles of incidence onto a grating electrode, thereby leading to a temperature difference between two sides of the quartz crystal wafer. Such a slight temperature difference may deform the wafer, and result in a frequency increase which can be easily read out by the QCM device.

The piezoelectric substrate may comprise a material selected from the group consisting of quartz (SiO$_2$), lithium tantalite (LiTaO$_3$), lithium niobate (LiNbO$_3$), potassium niobate (KNbO$_3$), Li$_2$B$_4$O$_7$, Berlinite (AlPO$_4$), The piezoelectric substrate may comprise a material selected from the group consisting of quartz (SiO$_2$), lithium tantalite (LiTaO$_3$), lithium niobate potassium niobate (KNbO$_3$), Li$_2$B$_4$O$_7$, Berlinite (AlPO$_4$), gallium orthophosphate (GaPO$_4$), Tourmaline, langasite (La$_3$Ga$_5$SiO$_{14}$), zinc oxide and/or epitaxially grown nitrides such as Al, Ga or Ln; Lanthandm gallium silicate, potassium sodium tartrate, barium titanate (BaTiO$_3$), Ba$_2$NaNb$_5$O$_5$, SrTiO$_3$, Pb(ZrTi)O$_3$, Pb$_2$KNb$_5$O$_{15}$, BiFeO$_3$, Na$_x$WO$_3$, lead zirconate titanate PZT. The piezoelectric substrate may also be a piezoelectric polymer such as polyvinylidene fluoride.

Any metal that is capable of resonating with light at a particular wavelength to produce a surface plasmon resonance may be used as the electrodes. Furthermore, the electrode is capable of conducting electrons to generate an electric field through the piezoelectric substrate or to receive an electric field generated by the piezoelectric substrate. In one embodiment, the electrodes may be non-reactive to the solvent within the fluid sample and may be non-reactive to oxygen, water, methanol ethanol and the like. In another embodiment, the electrodes may be fabricated from non-metal conductive materials such as Indium Tin Oxide (ITO). Advantageously, the electrodes are chemically inert to the fluid sample, to ensure that they are stable for analysis thereof The metal may be selected from the group consisting of Group IB, Group VIB, Group VIIIB, Group IVA, Group IVB, Group IIB and Group IIIA of the Periodic Table of Elements, as well as their alloys and combinations thereof.

In one embodiment, the metal may be selected from the group consisting of aluminum, cobalt, copper, gold, indium, molybdenum, nickel, palladium, platinum, silver, tin, titanium, tungsten, zinc and combinations thereof. In one embodiment, the metal is gold.

The metal may be deposited onto the surface of the piezoelectric substrate to form an electrode with a thickness selected from the group consisting of about 20 nm to about 2000 nm and about 80 nm to about 150 nm. It is to be appreciated that a person skilled in the art would understand that the choice of the thickness of the electrode depends on a number of factors such as transmittance of light by the electrode, cost of the metal and responsiveness of the piezoelectric substrate within the range at which the mass deposited is proportional to change in oscillation frequency of the piezoelectric substrate.

The surface of the piezoelectric substrate may be roughened. The rough surface may aid in the creation of surface plasmons on the piezoelectric substrate. This may be due to the diffraction of light into higher orders as it contacts the rough surface. In one embodiment, the surface of the piezoelectric substrate may be roughened via a periodic surface corrugation. In one embodiment, the surface of the piezoelectric substrate may comprise grating formations. The grating formations may be a series of parallel disposed grooves or slit formations provided on the surface of the piezoelectric substrate. The grating formations may be in the nano-scale range.

The grating formations may be formed on the surface by a method selected from the group consisting of photolithography, deep reactive ion beam etching, holographic lithography, e-beam lithography, ion-beam lithography, imprinting lithography and combinations thereof.

The grating constant of the grating formations on the surface of the piezoelectric substrate may be in the range selected from the group consisting of about 100 nm to about 1000 nm, about 100 nm to about 750 nm, about 250 nm to about 1000 nm, and about 400 nm to about 600 nm. In one embodiment, the grating constant is about 300 nm to about 750 nm. In another embodiment, the grating constant is about 520 nm. It is to be appreciated that a person skilled in the art would understand that the choice of the grating constant depends on a number of factors such as wavelength of the laser light and the medium through which the wavelength passes through, at which the incident angles are in the range for ease of alignment and detection.

The height/amplitude of the grating formations may be in the range selected from the group consisting of about 10 nm to about 100 nm and about 20 nm to about 35 nm. The metal electrode may be deposited onto the grating formations or may be stamped onto the piezoelectric substrate using a polymer substrate precoated with a metal layer. The polymer may comprise a material selected from the group consisting of polymethylmethacrylate (PMMA) and its derivatives, such as polyethylmethacrylate (PEMA), polypropylmethacrylate (PPMA), polybutylmethacrylate (PBMA) or a blend made of two or more thereof. The metal electrode may be deposited such that the shape and grating constant of the grating formations are substantially the same after deposition of the metal electrode.

In one embodiment, the surface of the metal electrodes may also be roughened in the same manner as the piezoelectric substrate as described above. In one embodiment, the metal electrodes have a periodic surface corrugation structure and are capable of detecting surface plasmon resonance when a light beam, such as laser light, is transmitted onto the piezoelectric substrate surface. The metal electrode is also capable of acting as a common surface for the detection of surface plasmon resonance measurement and determination of a gravimetric measurement. As a light beam is transmitted onto the metal electrode surface of an oscillating piezoelectric substrate (e.g. an AT-cut quartz crystal), the oscillation frequency of the substrate is detuned. The amplitude of the detuned frequency may be dependent on a number of factors such as light intensity, light wavelength, temperature of piezoelectric substrate, type of medium in contact with the piezoelectric substrate, non-reflective coating material on the metal electrode, etc. A detailed description will be provided further below with references to specific figures.

An important conclusion from the response of the AT-cut quartz crystal to the light illuminating on its front metal electrode is that the amplitude of the detuned oscillation frequency is proportional to the amount of the light energy transferred from the incident light to the metal electrode. This also applies to the case of the surface Plasmon resonance which is generated by coupling the incident laser beam to the metal-coated periodic corrugation surface when the momentum matching condition is fulfilled. The frequency response strictly correlates with the amount of reflectivity loss, and thus appearing as an inversed image of the conventional grating coupled surface Plasmon spectra. In this way, by measuring the change in the oscillation frequency of the piezoelectric substrate as a function of the angle of incidence, an optical signal (corresponding to the surface plasmon resonance detection) of the fluid sample can be obtained. In one embodiment, the oscillation frequency of the piezoelectric substrate may be used to detect both the surface plasmon resonance signal and a gravimetric signal at substantially the same time. The oscillation frequency may be measured at the fundamental frequency of the piezoelectric substrate, at the $3^{rd}$ overtone, at the $5^{th}$ overtone or at the $7^{th}$ overtone.

In another embodiment, a Kretschmann configuration may be used to couple the surface plasmon resonance to the piezoelectric substrate. The Kretschmann configuration may comprise an attenuated total reflection coupler placed adjacent to the fluid sample. The Kretschmann configuration may comprise light coupling medium disposed between the attenuated total reflection coupler and the sample to substantially match the refractive index of the attenuated total reflection coupler and piezoelectric substrate.

The attenuated total reflection coupler may be a prism having a shape selected from the group consisting of substantially hemispherical, substantially rectangular, substantially square, and substantially cylindrical.

The light coupling medium may be any transparent liquid that has a refractive index in the range selected from the group consisting of 1.50 to 1.60, 1.51 to 1.59, 1.52 to 1.58, 1.52 to 1.57, 1.52 to 1.56, 1.52 to 1.55 and 1.53 to 1.55. In one embodiment where the piezoelectric substrate is quartz, the light coupling medium may have a refractive index of about 1.54 at wavelength of 633 nm.

A cavity may exist between the piezoelectric substrate and the attenuated total reflection coupler, which may be filled with the light coupling medium and sealed. The distance, between the piezoelectric substrate and the attenuated total reflection coupler may be in the range selected from the group consisting of 0.5 mm to 2.5 mm, 0.75 mm to 2.25 m, and 1 mm to 2 mm. The light coupling medium may have a low density relative to that of water, the density may be within the range selected from the group consisting of 1.05 g/cm$^3$ to 1.3 g/cm$^3$, 1.1 g/cm$^3$ to 1.25 g/cm$^3$, and 1.1 g/cm$^3$ to 1.2 g/cm$^3$.

The light coupling medium may be an aqueous medium or a non-aqueous medium. In one embodiment, the light coupling medium is a hydrocarbon having carbon atoms in the range selected from the group consisting of 1 to 25, 2 to 20, 3 to 18, 4 to 15, 5 to 12, and 5 to 10. The light coupling medium may be selected from the group consisting of styrene, toluene, benzyl alcohol, and butylbenzene, tetrahydronaphthalene, acetophenone, benzonitrile, dibromomethane, benzylamine, 3-pyridinethethanol, 2-methylbenzenemethanamine, phenyloxirane.

The light beam may be transmitted from a halogen lamp, a light emitting diode, a fluorescent lamp or a diode laser. The light beam may be in the visible light region, the infra-red region or ultra-violet region of the Electromagnetic Spectrum. The light beam may be a laser beam. The laser beam may be emitted from a laser light source. The laser beam may be substantially s-polarized, substantially p-polarized or substantially unpolarized.

The wavelength of the light beam may be in the range of about 500 nm to about 1200 nm. In one embodiment, the wavelength of the light beam is about 543 nm, about 594 nm, about 633 nm or about 1150 nm.

The intensity of the light beam may be in the range of about 0.01 mW/mm$^2$ to about 100 mW/mm$^2$. In one embodiment, the intensity of the light beam in the form of a laser beam may be selected from the group consisting of about 0.014 mW/mm$^2$, about 0.029 mW/mm$^2$, about 0.057 mW/mm$^2$, about 0.0111 mW/mm$^2$, about 0.14 mW/mm$^2$, about 0.228 mW/mm$^2$, about 0.30 mW/mm$^2$, about 0.337 mW/mm$^2$, about 0.452 mW/mm$^2$ and about 0.568 mW/mm$^2$.

The transmitted light beam may be incident on a surface of the grating-furnished piezoelectric substrate and sweeps over a range of incident angles. The range of incident angles may be about 60° from the normal in the plus and minus directions, or from −60° to 60° in which mirror images will be obtained. It is to be appreciated that a person skilled in the art would understand that the choice of the range of the incident angles depends on a number of factors such as grating constant, wavelength of the laser light and the medium through which the wavelength passes through, ease of alignment and detection, at which surface plasmon resonance is achieved.

The sweep over a range of incident angles may be generated by the use of moving means. The moving means may comprise a motor that may be attached to either a light source for emitting the light beam or to the piezoelectric substrate. When the light beam is transmitted to the piezoelectric substrate, the moving means moves either the light source or the piezoelectric substrate relative to each other to thereby result in the light beam hitting the surface of the piezoelectric substrate at a plurality of incident angles.

The moving means may comprise a motor coupled to at least one light reflective material provided between the light source and the piezoelectric substrate. When a light beam is transmitted from the light source to the piezoelectric substrate, the moving means moves the light reflective material such that the light beam hits the surface of the piezoelectric substrate at a plurality of incident angles. In one embodiment, the light reflective material is a mirror. In another embodiment, as will be discussed in detail further below, two mirrors may be placed between the light source and the piezoelectric substrate with one of the mirrors being attached onto a motor.

At each sweep over a range of incident angles, the surface plasmon resonance and gravimetric measurements of the piezoelectric substrate may be measured.

The electrode may have a non-reflective surface. The non-reflective surface may be used to absorb the energy of the light beam and may result in higher response in oscillation frequency of the piezoelectric substrate, although it may not contribute to the amplitude of the detuned oscillation frequency of embodiments having an AT-cut quartz crystal induced by the surface plasmon resonance if a periodic surface corrugation presents and the resonance conditions are fulfilled. The non-reflective surface may be coated onto the electrodes or may be an inherent property the electrode. The non-reflective surface may be a dark color such as black. The non-reflective coating material may be silica or silica-based compounds. The silica-based coating material may be used to bind components of interest that are present in the fluid sample and hence, adheres the components of interest to the surface of the piezoelectric substrate.

In one embodiment, the reflective surface of the electrode may be diminished as the result of binding reactions that occurs between the components of interest that are present in the fluid sample and the electrodes. An increased amount of absorption of the energy of the light beam may result as more layers are being deposited on the electrodes during the binding reactions, due to diminished reflectivity. The increased absorption may result in a higher response in oscillation frequency of the piezoelectric substrate (higher baseline) and may serve as a semi-quantitative indication for the binding reactions.

The surface plasmon resonance measurement and the gravimetric measurement may be obtained at substantially the same time or may be obtained in a tandem manner, that is, one after the other. The surface plasmon resonance and gravimetric measurements obtained at substantially the same time may be subjected to further processing using analytical tools or software programs in order to distinguish between the two kinds of measurement.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Figure 1:
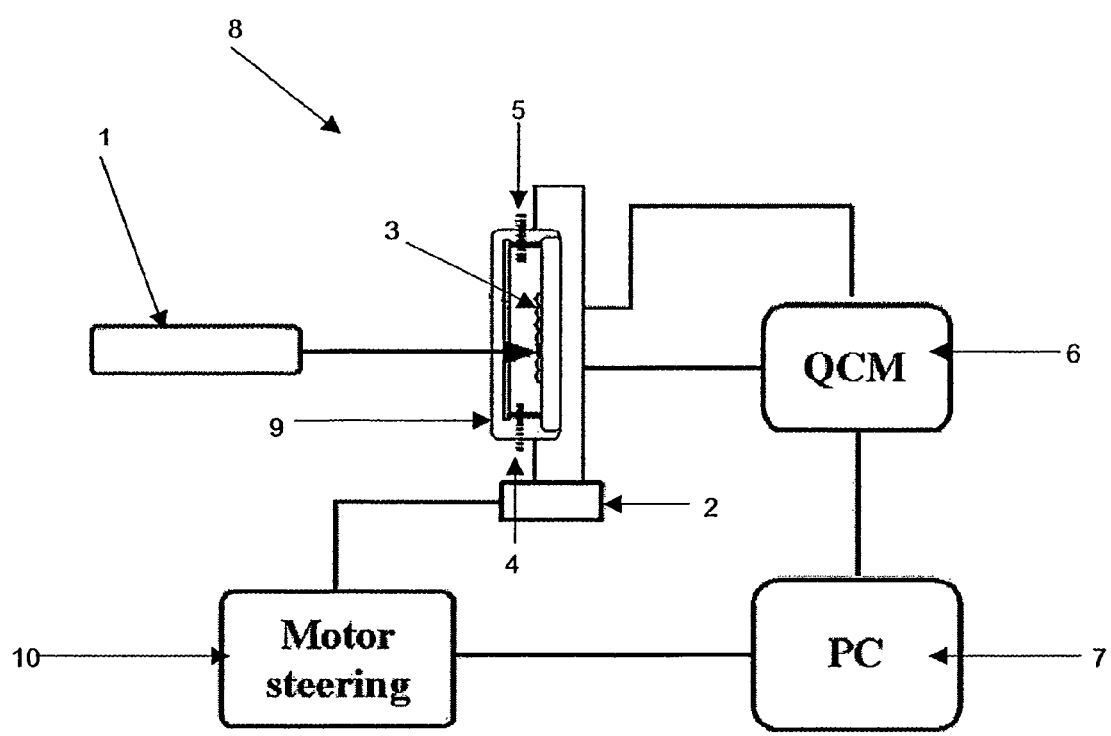
FIG. 1 is a schematic diagram of the setup of the system for Surface Plasmon Resonance and Gravimetric measurement as disclosed herein.

Referring to FIG. 1, there is shown a SPR and QCM (gravimetric) measurement system 8.

A flow cell 9 is used to contain a fluid sample and a piezoelectric substrate in the form of an AT-cut sensor quartz crystal 3. The sensor quartz crystal 3 was modified by a periodic surface corrugation (a grating structure) via photolithography plus ion milling. The gratings are prepared by developing a photoresist layer precoated on a quartz crystal wafer using the interference of coherent laser beams, in which one beam is the direct illumination of laser (half of the original beam) and the other is the reflection of the other half of same laser beam off a mirror. After the UV laser development, the substrate with photoresist grating structure is further etched using ion-milling to transfer the structure onto the quartz (etched into the quartz with a depth of 20~30 nm).

The grating constant, Λ, defined as the distance between two adjacent summits or valleys, can be tuned by varying the angle of the mirror to the original laser beam. The laser and substrate positions are fixed. The mirror is placed in a way to block half of the original laser beam, and can be rotated as need. The grating constant was fixed to Λ=520 nm for the convenience of the measurement. The reason using 520 nm is that for common Helium-Neon red laser (λ=633 nm) such grating constant allows the surface plasmon resonance angles for both air and other preferable fluid medium, such as water, buffers, alcohols, etc, to fall, into the incident angle range of −20 degrees to 20 degrees, which is easy for alignment and detection (due to the depth of the window cell, the accessible angle of the incidence is often limited). If laser wavelength is changed, a change of the grating constant is also needed.

The sensor quartz crystal 3 was coated by gold (not shown) on both sides. The gold coatings are able to act as electrodes for detecting changes in the oscillating frequency of the sensor quartz crystal 3. The flow cell 9 comprises an inlet conduit 4 and outlet conduit 5 for respectively allowing the inflow and outflow of the fluid sample to be analyzed.

The flow cell 9 is connected to a moving means in the form of motor-equipped rotary table 2 that rotates about a vertical axis driven by the motor steering device 10. The gold electrodes (not shown) that are present on either side of the sensor quartz crystal 3 are coupled to a frequency measurement means in the form of a QCM measuring device 6, which in turn is connected to a personal computer (PC) 7. The PC 7 is also electronically linked to the motor steering device 10. A light beam source in the form of a laser head 1 is situated near the flow cell and is controlled by a separate laser controlling device (not shown). The entire setup will be referred to hereafter as an "optics-integrated quartz crystal microbalance" or "O-QCM".

In operation, an amount of sample is passed through the inlet conduit 4. Excess or unwanted samples will exit from the flow cell 9 via the outlet conduit 5. The laser head 1 then emits a light beam in the form of a laser light towards the sample. The laser light passes through the sealing glass window and the transparent sample, prior to reaching the surface of the front gold electrode (not shown) of the sensor quartz crystal 3. Light energy from the laser light is transmitted to sensor quartz crystal 3 and detunes the oscillation frequency of the sensor quartz crystal 3. The amplitude of the detuned oscillation frequency is recorded via a QCM measuring device 6. When an interfacial event occurs, i.e., deposition of a layer of sample on the surface of the substrate sensor quartz crystal 3, a change in mass on the sensor quartz crystal 3 surface results in the shift in the oscillation frequency of the sensor quartz crystal 3. This shift is recorded in the QCM measuring device 6. This measurement of deposition of a layer of sample on the substrate sensor quartz crystal 3 is recorded as an "acoustic" signal. The PC 7 then activates the motor steering device 10 which results in the rotation of the sample rotary stage 2. The rotary table 2 rotates the sample flow cell 9 that is mounted on it over a range of incident angles. Hence the PC 7 indirectly controls the angle of incident light on the sensor quartz crystal 3. As the sample stage is moved through a series of different angles, the angle of incidence of the laser light varies form about −20° to about 20°. As the angle of incidence changes one moves in and out of the surface plasmon resonance, by which one varies the amount of the light energy coupled into the metal electrode of the sensor crystals. Accordingly, the amplitude of the detuned oscillating frequency of the sensor quartz crystal 3 follows the change. These changes of frequencies are subsequently detected by the QCM measuring device 6 and recorded in the PC 7. This measurement of changes of frequencies when the angle of incidence is varied is recorded as "optical" signals.

The entire process is repeated for different layers of samples that are deposited on the sensor quartz crystal 3 surface. From the change in frequency versus time graph that is generated by the PC 7, it is possible to obtain a conventional SPR curve and a conventional QCM curve concurrently.

Figure 2:
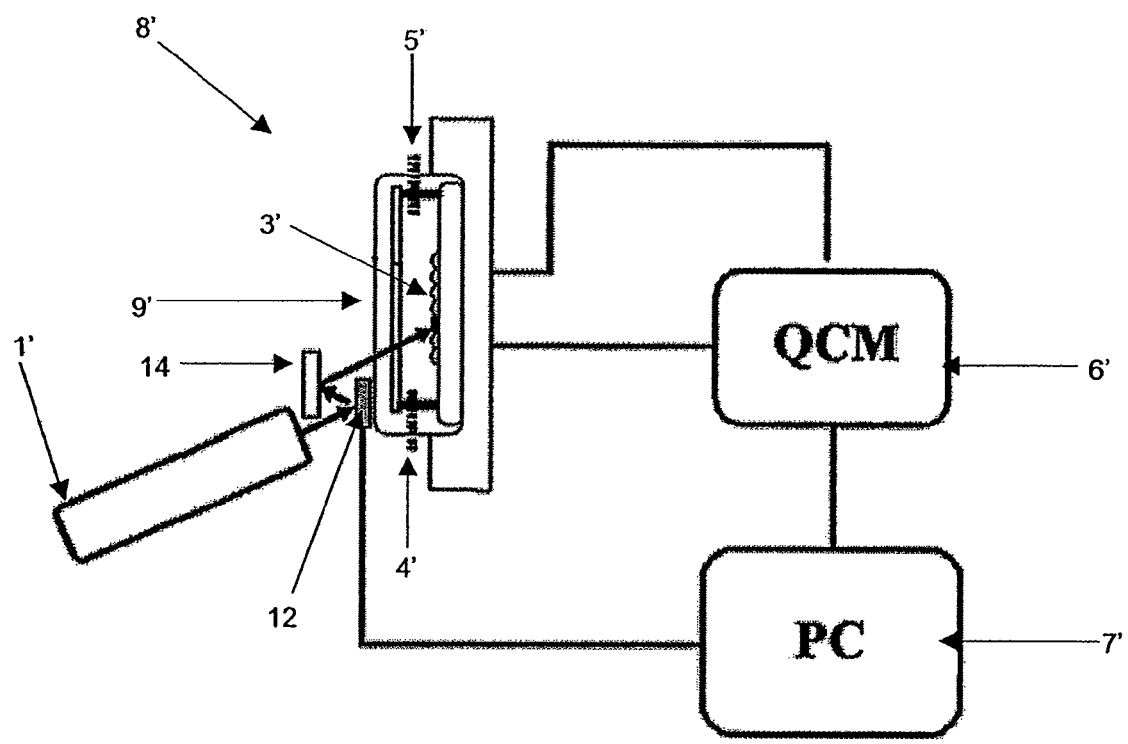
FIG. 2 is a schematic diagram of the setup of an alternative system for Surface Plasmon Resonance and Gravimetric measurement as disclosed herein.

Referring now to FIG. 2, there is shown a schematic diagram of an apparatus 8' having a number of technical features that, are the same as the apparatus 8 described above which are indicated by the same reference numeral but with a prime symbol ('). For example the system 8' comprises of a laser head 1', flow cell 9' (with a flow cell inlet 4' and a flow cell outlet 5'), a sensor quartz crystal 3', a QCM measuring device 6' and a PC 7', all of which are also present in the system 8. However, system 8' does not require the presence of a motor steering device 10 and a rotary table 2. Instead, system 8' further comprises a rotary mirror 12 and a stationary mirror 14. The combination of the stationary mirror 14 and the rotary mirror 12 of system 8' serves the same purpose as the rotary table 2 of system 8. When the rotary mirror 12 is rotated through various angles, the angle of incidence of the light on the sensor quartz crystal 13 surface also changes. Hence the process of operating system 8' to record both the "optical" and "acoustic" signals is Similar to system 8 as described above, with the exception that the rotary mirror 12 is rotated instead of a rotary table 2.

EXAMPLES

Systematic studies on the light-effect to quartz crystals were conducted, which includes the response of the quartz crystal to the change of light intensity, polarization, wavelength, pulse frequency if the light source is mechanically chopped; and the change of the coating materials (gold, silicon oxide, black painting) or their thickness on the front electrode of the quartz crystal on which the light incident, as well as the change of the medium (air, ethanol, water) in contact to the quartz crystal.

Figure 4:
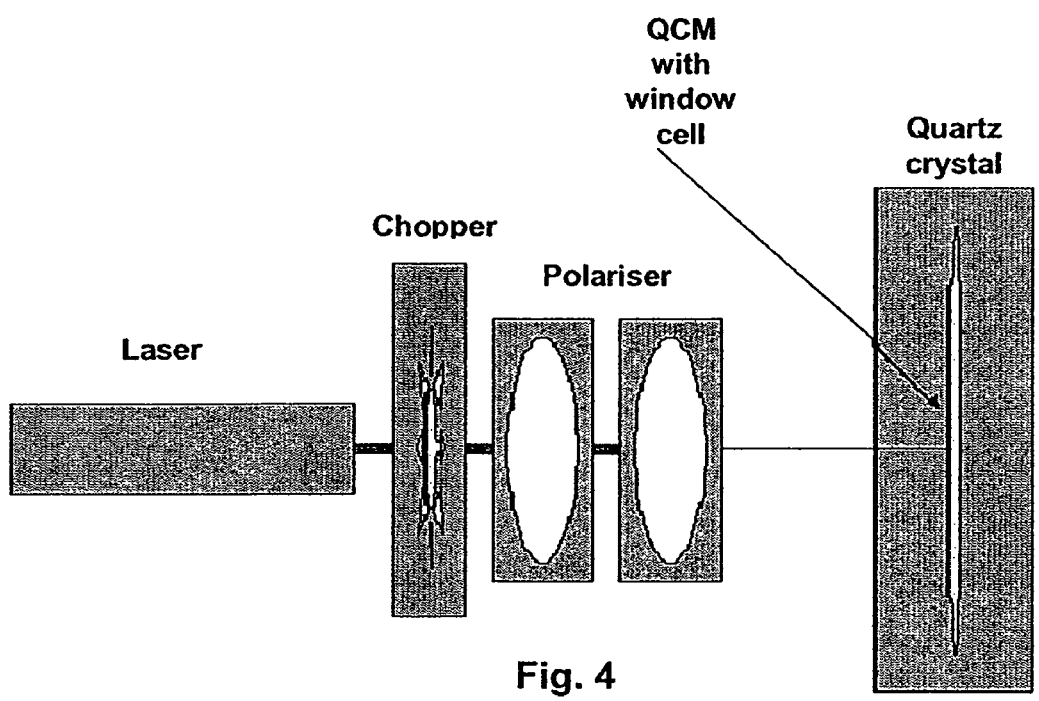
FIG. 4 is a schematic drawing of the setup used in the experiments disclosed below.

Furthermore, a QCM with a window cell was also used as detector for a surface plasmon resonance (SPR) measurement as shown in FIG. 4. Most of these experiments were carried out in air in order to minimize the disturbance of the environment, unless the medium in contact with the quartz crystal was of interest.

In some experiments, quartz crystals were AT-cut, sandwiched between a pair of gold electrodes with a gold or silicon oxide surface produced by Q-Sense AB (Sweden). Linearly polarized laser beams with similar intensities from Helium-Neon lasers with wavelengths of $\lambda=543$ nm (Research Electro-Optics, Inc., LHGP-0101), $\lambda=594$ nm (Melles Griot, 25-LYP-173-230), $\lambda=633$ nm (JDS Uniphase, 1125P), or $\lambda=1150$ nm (Research Electro-Optics Inc., LHIP-0201-115), respectively, incident on the front electrode of a sensor quartz crystal mounted in a window cell at normal incidence.

At a constant temperature of 25 degree Celsius the changes of the fundamental frequency as well as of the 3rd, 5th, and 7th overtones were recorded, except for experiments in which the QCM served as a photon detector. In this case a silica coated quartz crystal was used and only the signal of the 7th overtone was recorded.

Non-limiting examples of the experiments will now be further described in greater detail by reference to specific Examples and a specific Comparative Example, which should not be construed as in any way limiting the scope of the invention.

Example 1

Light Intensity Dependence

A direct and straightforward interpretation for this effect would be an energy-related phenomenon, and the shift in oscillation frequency could be laser intensity dependent. In order to test this hypothesis, light from a red Helium-Neon laser ($\lambda=633$ nm) with intensities of 0, 0.014, 0.029, 0.057, 0.111, 0.228, 0.337, 0.452, and 0.568 mW/mm$^2$, respectively (tuned by the relative polarization orientation of two polarizers and calculated from the laser power of 0, 0.1, 0.204, 0.404, 0.785, 1.61, 2.38, 3.192, 4.011 mW, respectively; the diameter of the laser spot was about 3.0 mm) was incident on the front gold electrode of the same quartz crystal at normal incidence and the frequency shifts were recorded accordingly. The temperature of the quartz crystal was constant (T~25° C.). All measurements were performed in air without the presence of a chopper.

Figure 3:
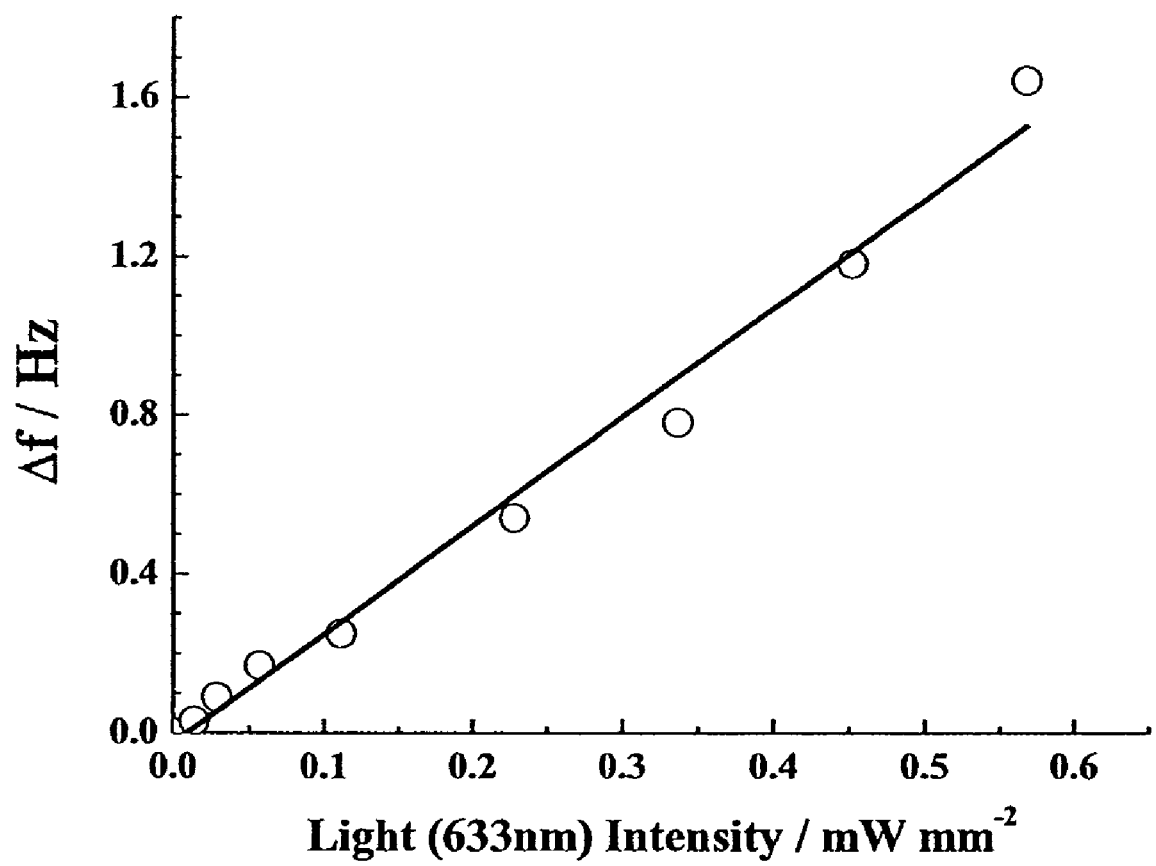
FIG. 3 is a graph of the frequency change of the quartz crystal versus intensity of light incident on the gold electrode of the crystal surface at normal incidence.

As a general rule, it was found that with the increase of the light input/intensity, the amplitude of the oscillation frequency shift became larger. Plotting the frequency increment against the intensity of the incident light (due to reflection and possible scattering losses the actual amount of light energy deposited on the quartz crystal was not clear; however, it should be proportional to the incident intensity), a straight line was found (FIG. 3) with some slight deviations which could be due to noise of the QCM, the inaccuracy of the light power measurement, as well as some unknown reasons.

This indicates an energy-related effect in which the oscillation frequency shift is proportional to the applied energy.

Example 2

Laser Pulse Frequency Dependence

The configuration of the experiment was such that a beam from a continuous Helium-Neon laser passed through a chopper (tuning the pulse frequency if necessary) and two polarizers (tuning the intensity and controlling the polarization of the final light if necessary), was incident on the front electrode of a quartz crystal with a fundamental frequency of ~5 Megaherz (MHz), mounted in a window cell produced by Q-Sense AB (Sweden) at normal incidence (FIG. 4).

Figure 5:
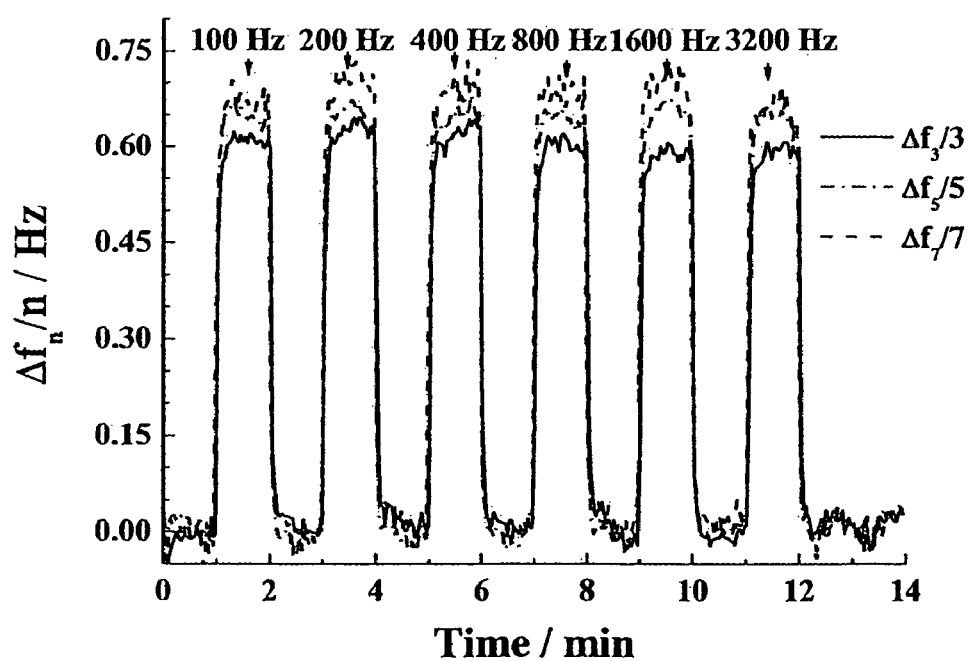
FIG. 5 are graphs of the phenomena observed for frequency change of a quartz crystal versus time when different pulse frequencies of the light source are transmitted to a piezoelectric substrate.

The laser pulse frequency was varied from 100 Hz to 3200 Hz (The pulse frequency was tuned while the laser beam was blocked. Due to limitations of the chopper higher pulse frequencies were not studied), and the response of the quartz crystal recorded accordingly (FIG. 5). The pulse frequency of the laser (chopper frequency) was changed during the period it was blocked. The temperature* of the quartz crystal was kept constant (T~25° C.). All measurements were performed in air, with the intensity of the red Helium-Neon laser ($\lambda=633$ nm) set at I=0.28 mW/mm$^2$. It can be seen that in FIG. 5, from 100 Hz to 1600 Hz, the difference in response of the quartz crystal in oscillation frequency was nearly undetectable. At a pulse frequency of 3200 Hz, a slight decrease was observed, however, this was still within the error range.

All these results appear to indicate that the pulse frequency, at least within the investigated range, did not play any key role in the increase of the oscillation frequency of quartz crystals.

A possible explanation is that the gold electrode layer is a very good thermal conductor, and the energy it adsorbs can be quickly (shorter than the case for the highest pulse frequency used—0.16 ms) dissipated into all directions within the plane of the electrode. With "continuous" (neglecting the pulse frequency) irradiation of the laser beam, a stationary flow of energy with a certain density (depending on the light intensity) was established through the electrode. As soon as the light was blocked, this flow disappears and the oscillation frequency of the quartz crystal returns back to the baseline level.

Example 3

Laser Polarization Dependence

The energy could be coupled to the quartz crystal as heat, or any other form of energy. In this case, a change of the polarization of the laser light should not cause any noticeable response, if the intensity of the beam is kept constant. Laser beams with s- or p-polarization was used. The temperature of quartz crystal was set as constant (T~25° C.). All the measurements were performed in air.

Figure 6:
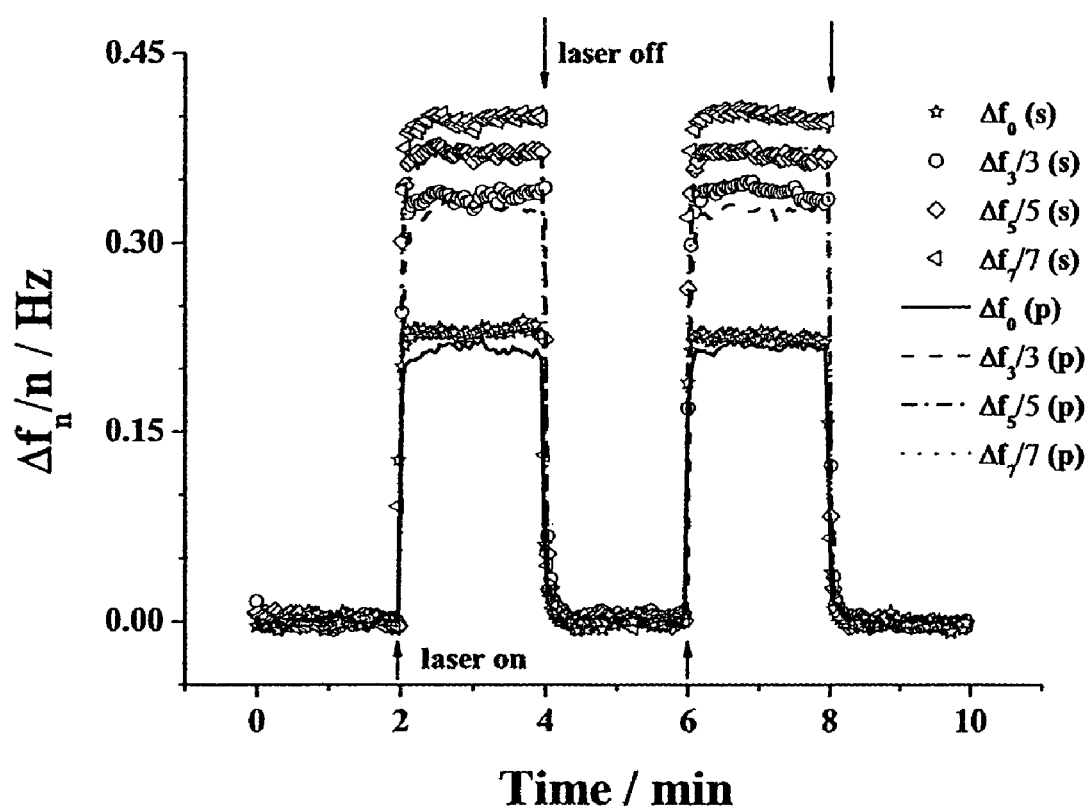
FIG. 6 are graphs of the amplitude of frequency change of quartz crystal versus time when different polarizations of light are used.

With intensity of the red Helium-Neon laser ($\lambda$=633 nm) I=0.14 mW/mm$^2$ and pulse frequency $F_p$=1200 Hz, the oscillation frequency of quartz crystal for s- and p-polarized light was studied, respectively, and the results are shown in FIG. 6.

Though the differences in the frequency response of quartz crystal are clearly seen between different modes (fundamental frequency and overtones or between different overtones), s-(symbols) and p-polarized (lines) light seem to induce the same change in the same oscillation frequency of the quartz crystal. This confirms that for a plain quartz crystal, the light effect has no preference for s- or p-polarized light.

Example 4

Laser Wavelength Dependence

Figure 7:
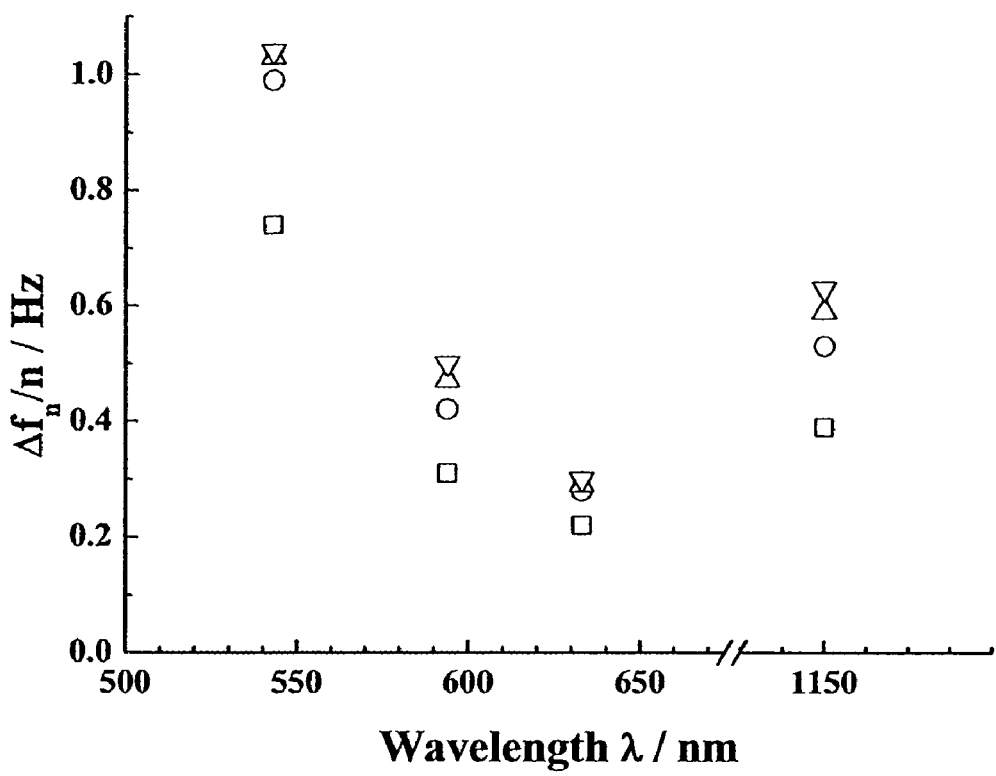
FIG. 7 is a graph showing the changes of the fundamental oscillation frequency (open squares) and the 3rd (open cycles), 5th (open up triangles) and 7th (open down triangles) of a gold-coated sensor crystal upon irradiation with laser beams of different wavelengths at I=0.14 mW/mm$^2$, F$_p$=1200 Hz.

The oscillation frequency response of the quartz crystal, however, was found to be irradiation wavelength dependent, if laser beams of different wavelengths with same intensity (as an example, an intensity of 0.14 mW/mm$^2$ was used in the experiments described here) were incident on the same sensor quartz crystal, respectively (FIG. 7).

From FIG. 7, one can see that from $\Lambda$=543 nm to $\Lambda$=594 nm to $\Lambda$=633 nm, the amplitude of the frequency shift decreases gradually.

However, with further increase of the wavelength to $\Lambda$=1150 nm, the amplitude of the frequency shift increases again. If one calculates the complex permittivity (dielectric constant) of the gold layers from their index of refraction at different wavelengths at 25 degrees Celcius, it can be seen that from $\lambda$=543 nm to $\lambda$=633 nm, the imaginary part of the dielectric constant ($\epsilon''$), mainly corresponding to the absorption, decreases from 1.886 to 1.328; while for $\lambda$=1150 nm this value is as large as 4.0664 (Table 1). The frequency response of the sensor quartz crystal upon irradiation with light of $\lambda$=1150 nm is for irradiation of different wavelengths. The penetration length of light into a material depends on the wavelength of the light, the ratio of the real and imaginary part of the dielectric constant (tan $\delta$=|$\epsilon''$/$\epsilon'$|), as well as the real part of the dielectric constant ($e'$).

Taking the empirical equation for microwave penetration $$d_p = \frac{\lambda}{2\pi \tan\delta \sqrt{|\varepsilon'|}}$$

as a raw estimation, one can see that the penetration length increases with the increase of the light wavelength. A further approximation is done by averaging the absorbed energy ($\epsilon''$) over the penetration length evenly for each individual wavelength. As can be seen from Table 1, the values correlate well with the frequency response data displayed in FIG. 7.

TABLE 1

Calculated optical parameters of gold layers at different wavelengths.

| $\lambda$/nm | n | κ | $\epsilon'$ | $\epsilon''$ | $d_p$/nm | $\epsilon''/d_p$ |
|---|---|---|---|---|---|---|
| 543 | 0.41 | 2.30 | −5.1219 | 1.886 | 103.8 | 0.01817 |
| 594 | 0.24 | 2.90 | −8.3524 | 1.392 | 196.4 | 0.00709 |
| 633 | 0.20 | 3.32 | −10.9824 | 1.328 | 251.6 | 0.00528 |
| 1150 | 0.26 | 7.82 | −61.0848 | 4.0664 | 351.8 | 0.01156 |

($\epsilon = \epsilon' + i\epsilon''$)

Example 4

Thermal Effect by Heating the Cell

Figure 8:
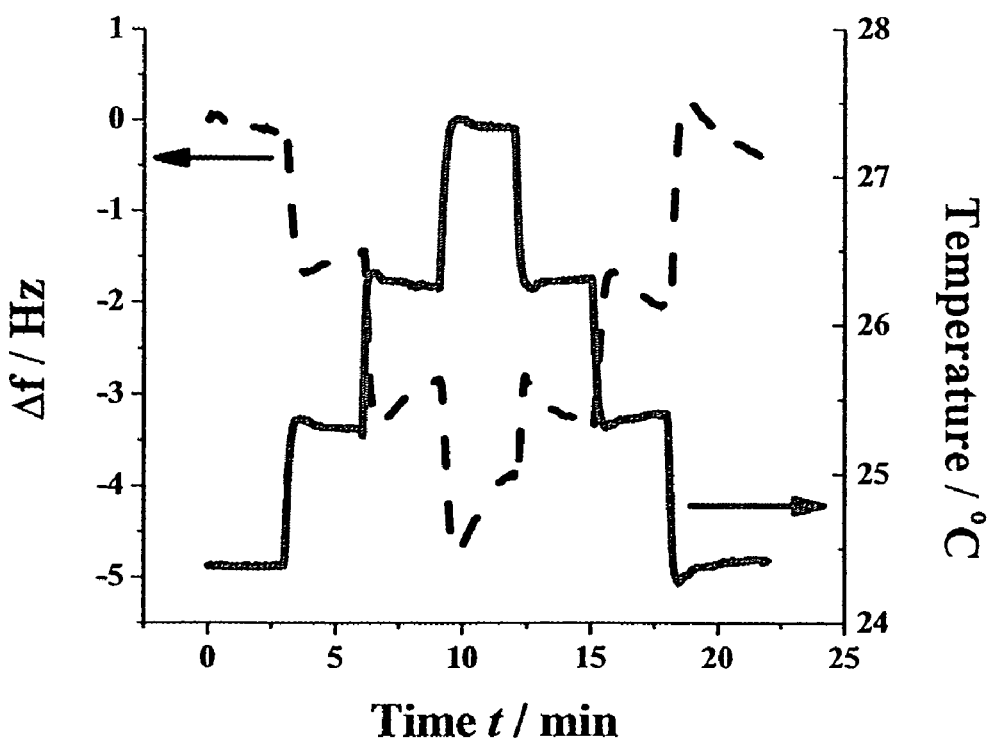
FIG. 8 is a graph showing the oscillation frequency response (dash line) of a gold-coated sensor crystal upon temperature changes (solid line).

The correlation of the frequency shift with the laser input and the wavelengths seems to suggest a thermal effect. However, in case that the whole cell was heated, an opposite response (a frequency decrease) was observed (FIG. 8). This indicates that the change of the sensor crystal frequency under light irradiation is not simple thermal effect by (isotropic) heating. Considering the good thermal conductive property of gold (317 W/m/K at room temperature), the possibility of a (lateral) temperature difference on the gold electrode on one side is rare.

Nevertheless, the much smaller thermal conductivity of the quartz crystal (12 or 6.8 W/m/K for parallel or perpendicular to the c axis) in comparison to gold makes it possible to have a slight temperature difference between the two sides of the quartz crystal, leading to some mechanical stress and thus a frequency increase. An enlarged effect was seen by applying light irradiation of high power (a few Watts) onto the quartz crystal: in the experiment the crystal sensor stopped oscillating as soon as such strong light reached its front electrode surface.

Example 5

Medium in Contact with the Crystal

Figure 9:
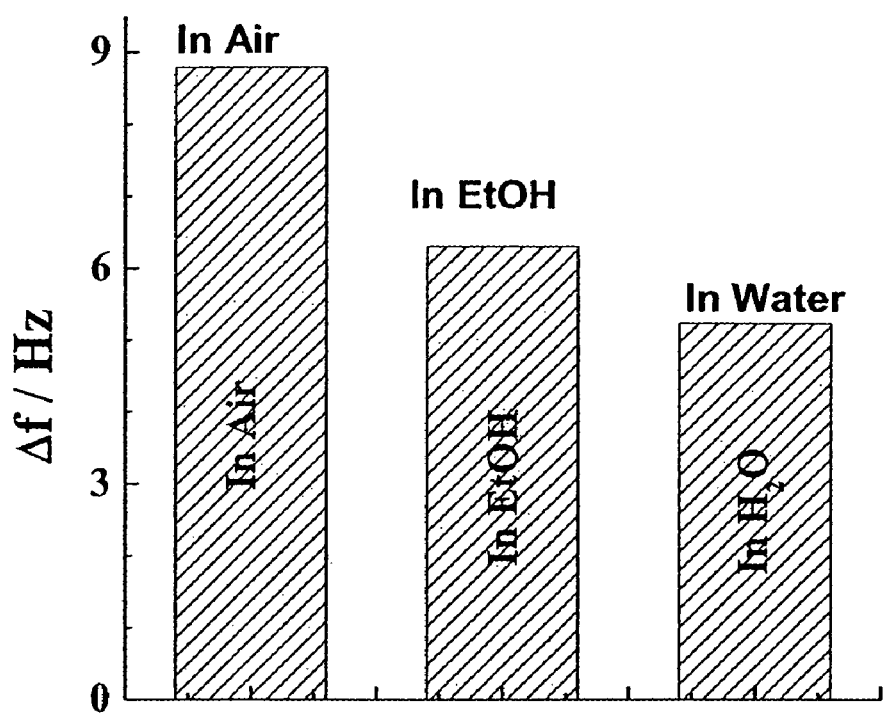
FIG. 9 are bar charts depicting the oscillation frequency response of a gold-coated sensor quartz crystal upon irradiation of a Xenon lamp in the presence of air, ethanol and water, respectively.

More evidence for the temperature difference induced stress comes from experiments in which water or ethanol is used as medium in the cell instead of air. In order to illustrate the phenomena more clearly, light with a larger energy, input from a Xenon lamp was used as the irradiation source. The results are shown in FIG. 9.

The frequency response for sensor crystals in three different media upon irradiation with the same input were in the order: $\Delta f_{air}$=8.8 Hz>$\Delta f_{ethanol}$=6.3 Hz>$\Delta f_{water}$=5.2 Hz. This can be well understood on the basis of the thermal conductivities of air, ethanol and water being 0.0262, 0.169 and 0.6071 W/m/K, respectively.

The water environment with the best thermal conductivity among the three lowered the temperature difference to the largest extent, thus inducing the lowest mechanical stress and, hence, the smallest frequency shift. The heat absorbed by the liquid medium close to the surface of the sensor crystal is larger if the thermal conductivity is smaller (in the case of ethanol). With a smaller specific thermal capacity ($C_{p,ethanol}$=2.48 J/g/K<$C_{p,water}$=4.178.4 J/g/K), the temperature change of the liquid medium is assumed to be larger in the case of ethanol as environment. This is in good agreement with the decrease of the dissipation factor for the larger frequency response ($0.72 \times 10^{-6}$ for ethanol in comparison to $0.36 \times 10^{-6}$ for water) corresponding to a more pronounced decrease in the viscosity.

Example 6

Surface Coating Materials

Figure 10:
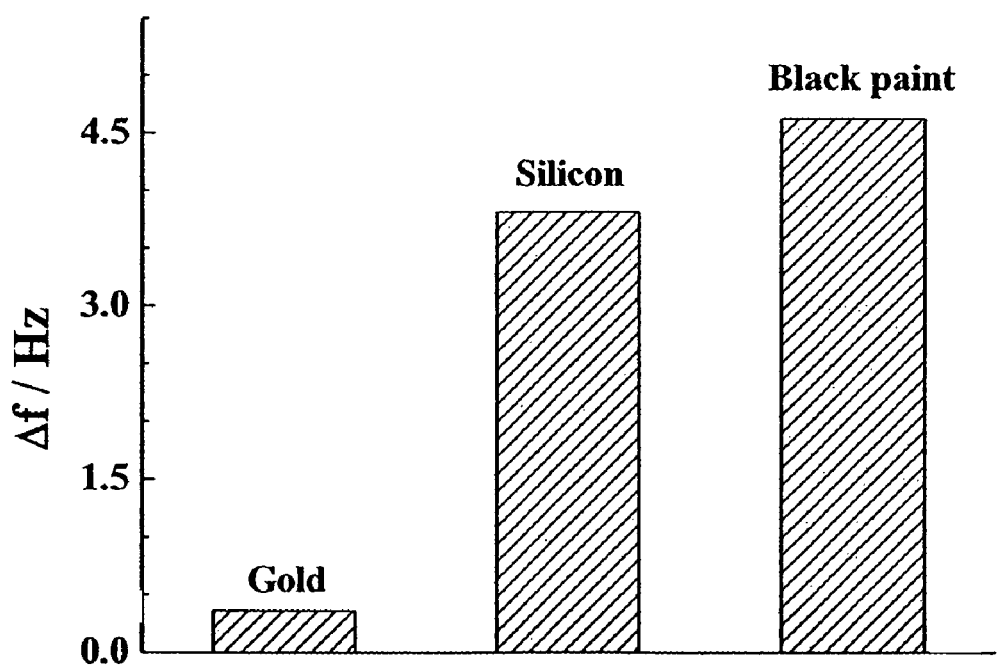
FIG. 10 are bar charts showing the oscillation frequency response of a sensor quartz crystal with the surface of front electrode being gold, silica and black painting, respectively.

If a solid material (e.g., $SiO_2$) is coated onto the quartz crystal, the reflection of the beam is reduced. In this case, more energy accumulates on the front electrode of the sensor quartz crystal. Correspondingly, a several times larger response was observed (FIG. 10). This applies to light of different wavelengths (although for the red laser it was the most pronounced).

It is noteworthy that the responses of the silicon oxide surface to light of different wavelengths are rather similar. This should be due to the non-selective character of the silicon oxide surface to light within the above wavelength range.

Further tests conducted were the deposition of a second gold layer onto the already gold-coated electrode. 40 and 80 (40+40) nm of gold was deposited on the same crystal, in succession and the oscillation frequency response of the quartz crystal was studied after each deposition. In these experiments, the temperature of the quartz crystal was constant (T~25° C.) and the measurements were performed in air, with the intensity of the red. Helium-Neon laser ($\lambda=633$ nm) I=0.14 mW/mm² and a pulse frequency $F_p=1200$ Hz.

No noticeable difference was observed in the frequency response for these two cases. However, coating the gold electrode of a quartz crystal with black paint led to an even higher oscillation frequency response (FIG. 10). This supported the hypothesis that a less reflective surface results in a higher response in oscillation frequency of the quartz crystal.

Example 7

QCM as a Detector for Surface Plasmon Resonance Spectroscopy

Figure 11:
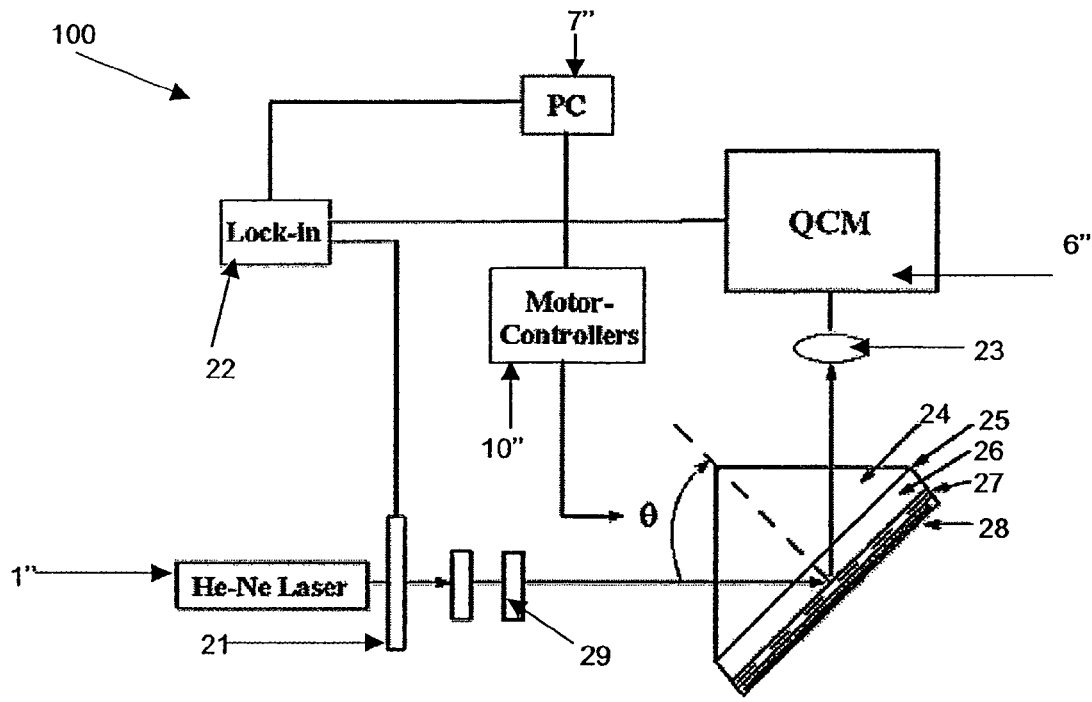
FIG. 11 is a schematic diagram of the configuration of the experimental set-up in which quartz crystal is demonstrated as a detector for a home-built surface plasmon resonance spectrometer.

FIG. 11 is a schematic diagram of an apparatus 100 having a number of technical features that are the same as the apparatus 8 described above which are indicated by the same reference numeral but with a double prime symbol ("). As shown in FIG. 11, a Helium-Neon-Laser 1" (1105P, $\lambda=633$ nm, Uniphase) with a power of 5 mW was used as the light source. The laser beam was modulated by a mechanic chopper 21, and passed through two polarisers 29 (PGT28, Halle), before it reached the highly refractive coupling LaSFN9 prism 24 (Spindler & Hoyer) and the index-matched sample LaSFN9 slide. The prism 24 which is in contact with a layer of immersion oil 25, is coupled to glass substrate 26 which rests on a metal layer 27 with dielectric coatings 28. The reflected beam was monitored by a quartz crystal with frequency read out. A lock-in amplifier 22 is kept as it is in a conventional surface Plasmon resonance spectrometer, but without any function in the demonstrated measurement here. Sample and detector stages are mounted in a two-circle goniometer, operated in a θ/2θ mode.

Figure 12:
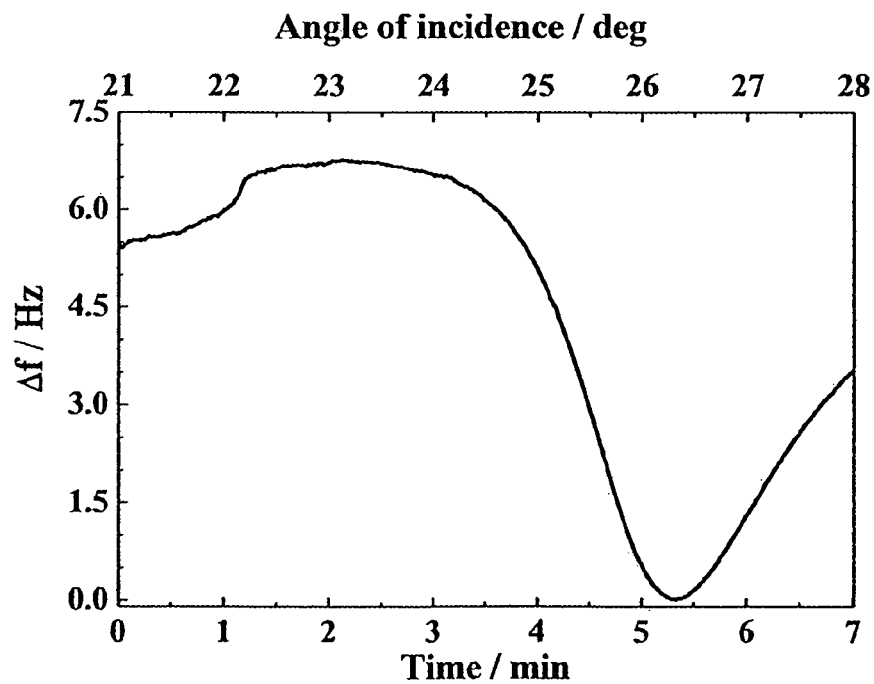
FIG. 12 is a graph that shows the experimental curve for an optical scan recorded by a quartz crystal instead of a conventional photodiode detector.

In this example, as one sweeps the angle of incidence for the laser beam on the sample (substrate at the base of the rectangular prism) over the range of 21 to 28 degrees, three stages should be visible. Below the critical angle $\theta_c$, a reflectivity of about 80 percent with slow increase towards higher angles is seen due to the mirror reflection by the metal layer coated on the substrate; at $\theta_c$ total internal reflection occurs and the reflectivity reaches its maximum; above $\theta_c$, the reflectivity stays at the maximum for a while before a fast decrease is seen upon the excitation of the surface Plasmon resonance. The reflectivity reaches its minimum at the resonance angle ($\theta_r$) and increases again for incident angles larger than $\theta_r$, as shown in FIG. 12. All three stages are clearly visible, proving the successful application of quartz crystal as photo-detectors. It is to be appreciated that the angle sweep may be in the range of 20 to 80 degrees in other examples.

Example 8

Figure 13:
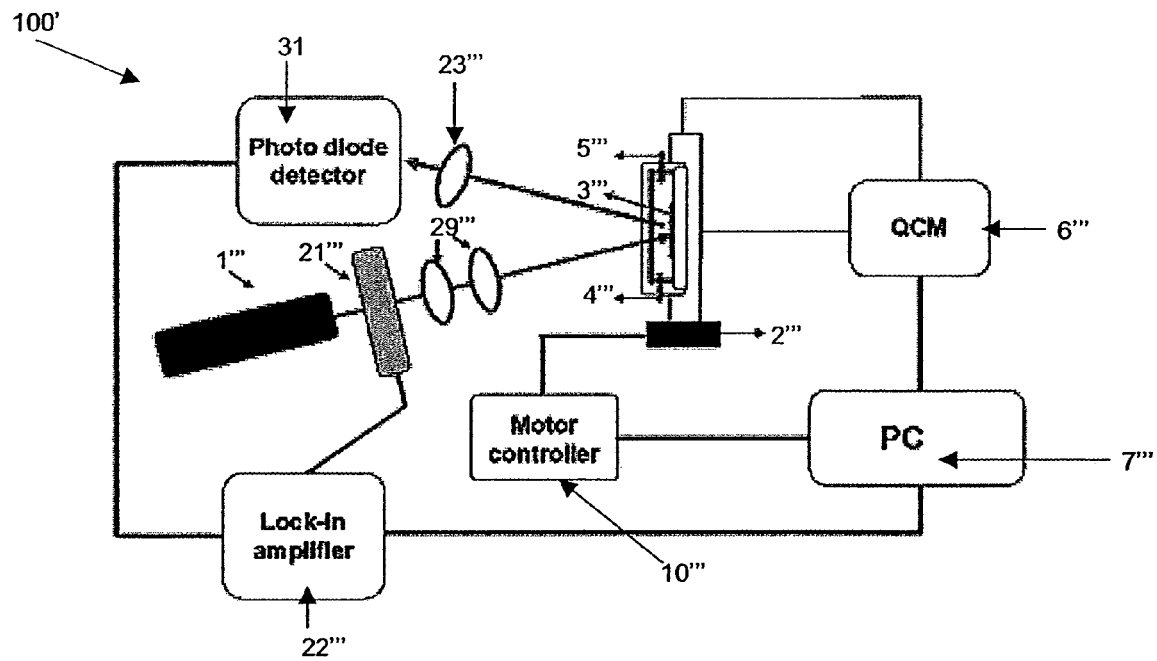
FIG. 13 is a schematic drawing of a grating-coupled surface plasmon resonance spectrometer and quartz crystal microbalance combination set-up used in comparative example 1 described below.

Measuring the Frequency Response on QCM Upon Surface Plasmon Resonance from Periodic Surface Corrugation Structure on AT-cut Quartz Crystal Electrode Surface The configuration for the combination of a grating coupled surface plasmon resonance (SPR) spectrometer and a quartz crystal microbalance was used as depicted in FIG. 13. FIG. 13 is a schematic diagram of an apparatus 100' having a number of technical features that are the same as the apparatus 100 (FIG. 11) described above which are indicated by the same reference numeral but with a triple prime symbol (' ").

In comparison to the prism coupled SPR spectroscopy in which light is coupled from the backside of the gold film, in grating SPR (G-SPR) the coupling process takes place at the front side of the gold layer. In a G-SPR/QCM combination set-up, it is the front electrode where the SPR detection happens. The same front electrode is also the platform on which deposition/desorption of a layer or other surface/interfacial events take place and are presented as changes in the frequency and/or dissipation. This common surface of interest allows for an easy detection of both SPA (optical) and QCM (acoustic) signals simultaneously.

In the present experiment, the environment of the quartz crystal was air, and an angular scan using much higher laser intensity (in comparison to the standard SPR measurement) was performed. The reflectivity detected by the photodiode detector 31 and the responses of the quartz crystal (frequency change) were recorded.

Figure 14:
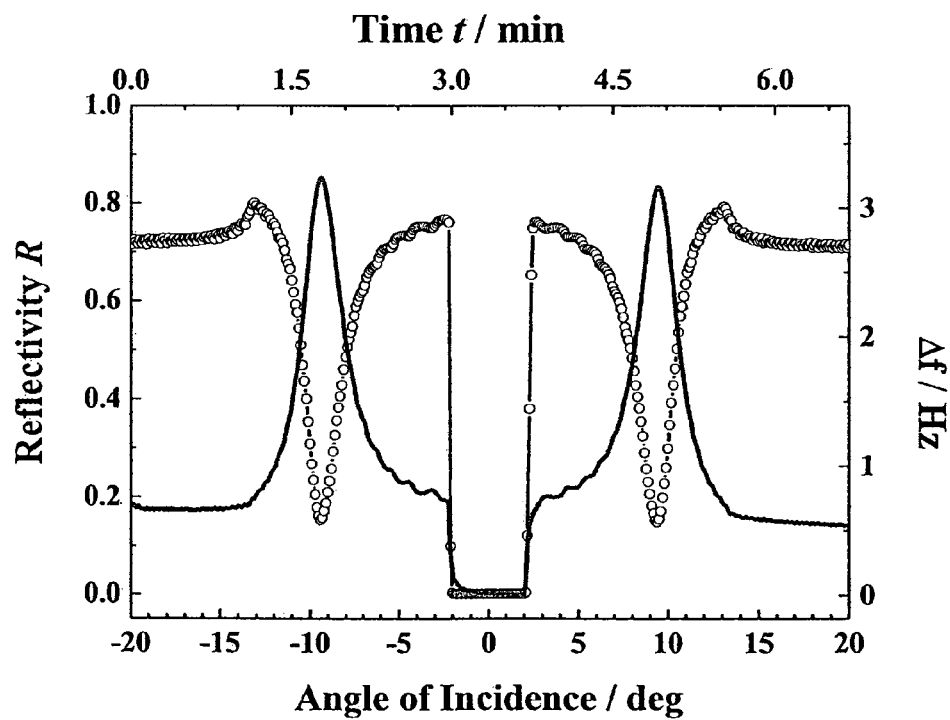
FIG. 14 is a graph of frequency response (solid curve) of a sensor quartz crystal with a grating structure (Λ=520 nm) to the excitation of a surface plasmon (open circles and solid straight line) by light of λ=633 nm, p-polarized, I=0.14 mW/mm$^2$, F$_p$=1200 Hz.

The laser beam intensity used was about 30 times of what is used in a conventional surface plasmon resonance spectroscopy and the scanned angle range was from −20° to 20° (in grating-coupled SPR two resonance dips appear symmetrically to normal incidence). The simultaneously recorded SPR curve and the frequency change are shown in FIG. 14.

It was found that the frequency response correlated strictly with the surface plasmon reflectivity loss at all angle of incidence, except for incident angles larger than the critical angle (13°→20° and its mirror image (−20°→13°, respectively. In these two angular regions light is diffracted into the −1st/+1st diffraction order, respectively, with a concomitant loss of reflected intensity. This, however, does not result in a change in the deposited energy and, hence, the frequency response changed little. With the angle of incidence gradually reaching the surface plasmon resonance (starting at ~−13°, the oscillation frequency begins to increase visibly. At the resonant angle (−9.7° it reaches the maximum. For angular range for which the light was blocked (−2°→2°, the change of the frequency dropped to 0. A symmetric scan at the positive region (0°→20° gave similar results. This suggests that the surface plasmon resonance signals (reflectivity loss) can be represented by the frequency increase on QCM, thus enabling the recording of the surface plasmon resonance with acoustic signals, i.e. a curve with an inversed shape to a conventional grating surface plasmon resonance curve, but with frequency vs time as axes instead of the conventional reflectivity vs the angle of incidence. Together with the intrinsic acoustic detection of the QCM, one can furnish a set-up with full function of a G-SPR/QCM combination set-up, but in a much simpler configuration (FIG. 1) which may be named as "optics-integrated quartz crystal microbalance", or in short "OQCM".

Example 9

Demonstrating the Utility of the OQCM Set-up Using Well-Documented PDADMAC/PSS Bilayer Formation System Poly(diallyl dimethyl ammonium chloride) (PDADMAC), poly(styrene sulfonate sodium) (PSS), 3-mercapto-propyl-sulfonate sodium (MPS), concentrated sulfuric acid (99%), hydroperoxide aqueous solution (30%) were all Aldrich products. The concentration for both polymers were 0.01 M with extra added ion strength of 0.18 M, prepared by diluting 0.1 M polymer aqueous solution with 9 times (v/v) of 0.2 M PBS buffer. In this experiment, the setup as shown is FIG. 1 was adopted.

A gold-coated quartz crystal with a grating structure ($\Lambda$~520 nm) was treated with a UV-ozone cleaner for 5 minutes, followed by a treatment in $H_2SO_4/H_2O_2$ (3:1) for 10 minutes. After rinsing with milli-Q water (18.2 M$\Omega$ cm) and drying in a stream of dry nitrogen, the quartz crystal was mounted into the window cell and an in-situ functionalization with MPS was performed in order to get a negatively charged surface.

After rinsing, signal recording was started. Laser light of $\lambda$=633 nm, p-polarized, I=0.50 mW/mm$^2$. After the baseline stabilization, a fine angular scan from 0° to 25° (stepsize: 0.1°) was taken, while both the starting and ending time of the scans was noted. A frequency feature with a shape inverse to a regular SPR curve (FIG. 15, cf. also FIG. 14) was found. While the scan motor was driven back to the starting position (0°) quickly, a narrow and sharp peak with a lower frequency response was seen. This can be seen as a repetition of the angular scan but with a much faster scan rate. After a few minutes, the 0.01 M aqueous PDADMAC solution with an ionic strength of 0.18 M was injected into the cell via a peristaltic pump at a flow rate of 0.5 mL/min. A fast decrease of the frequency was observed as soon as the PDADMAC reached the quartz crystal surface. About 15 minutes after the PDADMAC feeding a new stable baseline was reached. PBS buffer with an ionic strength of 0.18 M was then pumped into the cell in order to remove any excess amount of free PDADMAC while keeping the liquid environment of the quartz crystal unchanged (in order to avoid any buffer (exchange) effects).

Then, another angular scan was performed. Through the PDADMAC deposition, the surface of the quartz crystal became positively charged which allowed for the deposition of a layer of PSS, monitored as a frequency decrease of the OQCM signal. After PSS layer deposition, the angular scan recording was repeated. By several cycles of alternate polyelectrolyte depositions, films of virtually any desired thickness can be prepared. As an example, the deposition protocol of a polyelectrolyte film with two PDADMAC/PSS bilayers on the OQCM is shown in FIG. 15.

Figure 18:
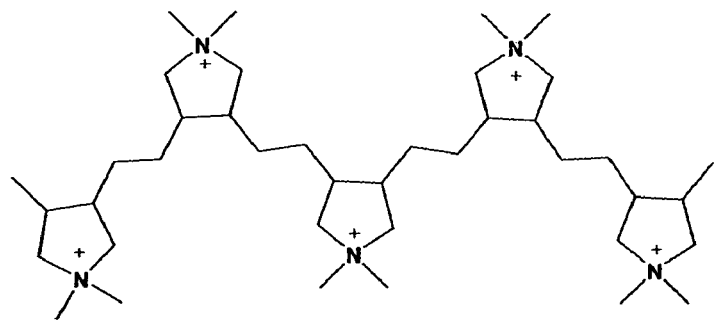
FIG. 18*a* is an illustrative drawing of the chemical structure of PDADMAC, with the small counterions (chloride ions) deliberately omitted.
FIG. 18*b* is an illustrative drawing of the chemical structure of PSS, with the small counterions (sodium ions) deliberately omitted.
Figure 18:
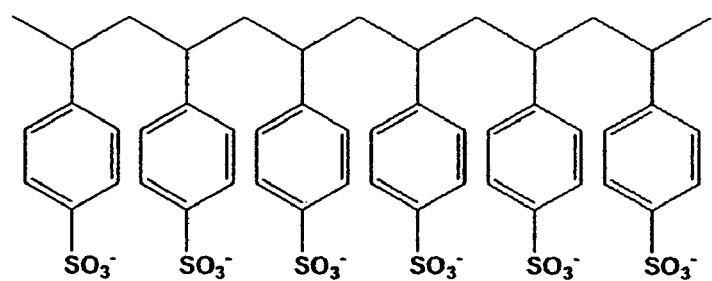

Polyelectrolyte layer-by-layer deposition has been well studied and documented and thus can be taken as a calibration for the new system. The reasons for choosing PDADMAC and PSS are: i) these polymers are oppositely charged and easily available ii) they possess different packing density (cf. their chemical structure given in FIG. 18a and FIG. 18b) thus giving rise to different amounts of incorporated water upon forming coils at high ionic strength which may result in interesting differences between the acoustic and the optical signals.

Figure 15:
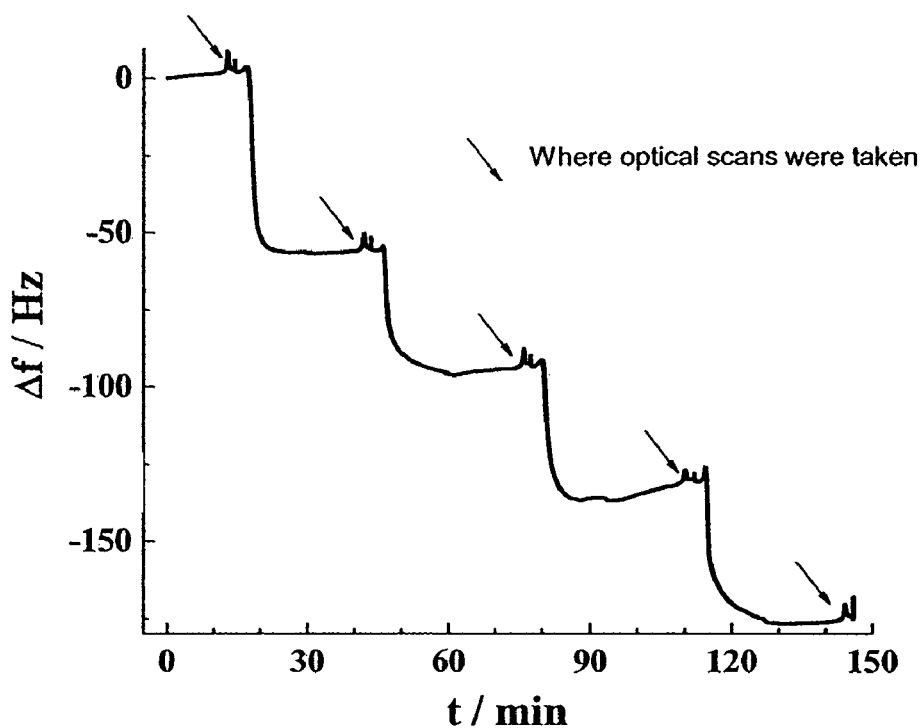
FIG. 15 is a graph showing the deposition trace of 2 PDAD-MAC/PSS bilayers onto a negatively charged surface recorded by the Optics-Integrated Quartz Crystal Microbalance.

The acoustic information, i.e. the frequency decrease $\Delta f$, upon the deposition of each individual layer can be directly read from FIG. 15 and yields. $\Delta f$=57.6, 38.1, 37.7 and 43.9 Hz for the deposition sequence of PDADMAC-PSS-PDADMAC-PSS layers, respectively. It seems that the reproducibility of the frequency change for each deposition of the same polyelectrolyte layer was not very good, with not much difference between PDADMAC and PSS.

Figure 16:
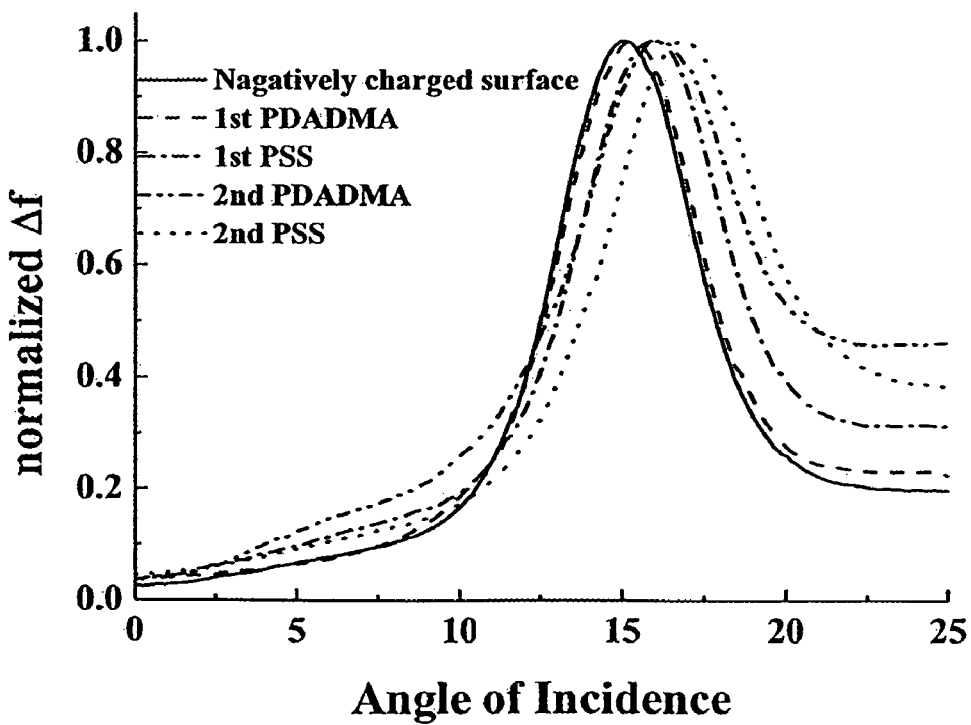
FIG. 16 are graphs showing optical information converted from the O-QCM kinetic data. Scans were taken before and after the deposition of each individual layer.

Extracting the frequency change and the time data for the angular scans from FIG. 15, and setting the time for the starting point of each scan as t=0. The time columns were then normalized, and multiplied by the widths of angles scanned (25 in this case). By such treatment (time-to-angle conversion) the frequency response as a function of the angle of incidence, i.e. the optical information, was obtained. Since the peak position (corresponding to the SPR dip) is the sole important parameter for the optical data analysis, all frequency changes for different scans were normalized for better comparison. Data for all five scans were then plotted together in FIG. 16. In FIG. 16, three tendencies are visible: i) after each film deposition, the peak of the curve shifted to higher angles of incidence (same as in SPR), which corresponds to a later occurrence in the original data recorded on OQCM; ii) the shift for each layer of the same material is similar; and iii) the shift for the denser packing material PSS is apparently larger than that for the looser packing material PDADMAC.

Figure 17:
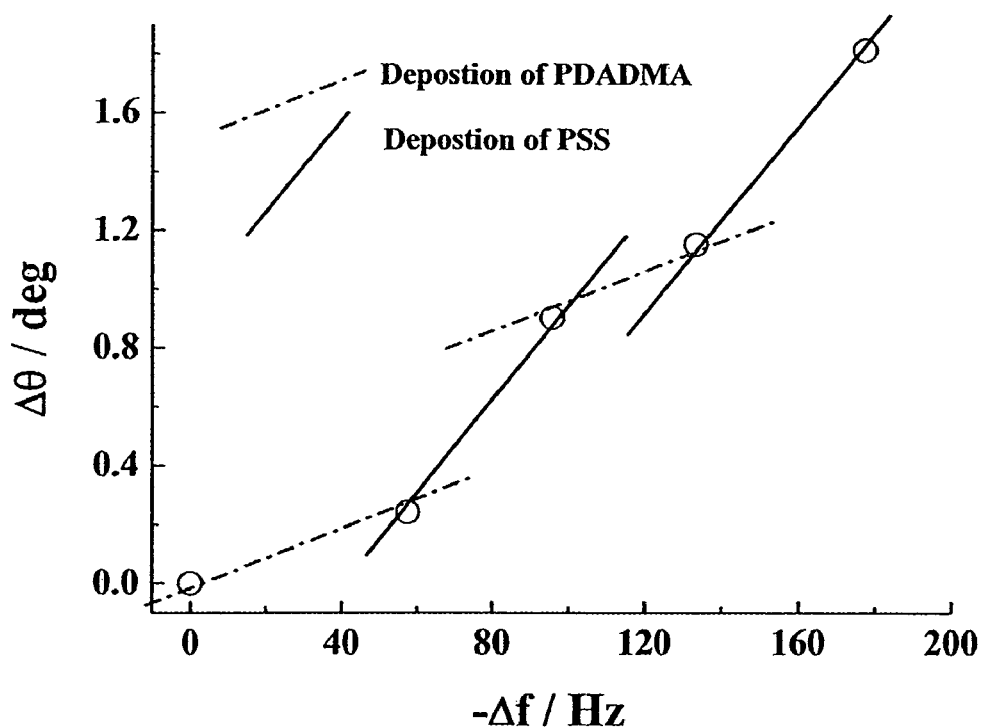
FIG. 17 are line charts showing shifts in angle of incidence against decrease in oscillation frequency for the deposition of individual layers of two polymers: PDADMAC and PSS.

A more detailed data analysis gives the values of the angle shifts for the 4 individual layers (PDADMA, PSS, PDADMAC, and again PSS) as: 0.24°, 0.56°, 0.25°, 0.56°. This optical information suggests a very good reproducibility on the same layer deposition. A plot of the optical signals against the acoustic ones is shown in FIG. 17, in which it can be seen that the deposition of PDADMAC and PSS can be fitted with two different slopes (same slope was used for the same polyelectrolyte in different deposition cycles). However, the slope for PDADMAC deposition is much flatter in comparison to that of PSS, suggesting a less densely packed film with larger amounts of solvent incorporated. This fits well into the image drawn from the molecular structure (cf. FIG. 18a and FIG. 18b).

Applications

The disclosed surface plasmon resonance and gravimetric sensing method and system may be used for a variety of applications in pharmaceutical industries, research, medical diagnostic testing, detection of biologics or microorganisms for food safety or security purposes (such as bio-terrorism monitoring) or in environmental monitoring. These applications may comprise ligand screening, immunology, cell biology, signal transduction, chemical interactions and nucleotide-nucleotide, nucleotide-protein, protein-protein and protein-lipid interactions.

The disclosed surface plasmon resonance and gravimetric sensing method and system may be used as biosensors for in-situ, label free analysis of binding reactions.

The disclosed surface plasmon resonance and gravimetric sensing method and system may be used for detecting ultrathin rigid layer formation or removal, such as thin film deposition or growth of metals, inorganic, organic, bio-compounds or polymers at ambient or elevated pressures. The detection of rigid layer formation can be obtained at the surface of the piezoelectric substrate or at the interfacial layer between two fluid phases. The sample material may be adsorbed onto the surface of the piezoelectric substrate, deposited onto the surface via vapour deposition in vacuum or at ambient pressures, chemically bonded to the surface as a result of a chemical reaction occurring at the surface or as a result of electrostatic interaction.

The disclosed surface plasmon resonance and gravimetric sensing method and system may be used as an analytical tool for studying the formation and behavior of viscoelastic layers of a sample material in a liquid environment in order to determine both the surface plasmon resonance (optical) measurement and gravimetric (mass) measurement.

The disclosed surface plasmon resonance and gravimetric sensing method and system enable the monitoring of same interfacial phenomena at exactly the same surface using two fundamentally different measurement techniques simultaneously or in a tandem mode. The complementary surface plasmon resonance and gravimetric or quartz crystal microbalance signals acquired from the piezoelectric substrate take advantage of the strengths of each sensing technique.

Advantageously, the disclosed method and system may be capable of generating substantially accurate and reproducible experimental results as compared to conventional techniques. For example, in one embodiment, the problem associated with light interference as a result of reflected light from the sample cell in conventional techniques is substantially eliminated in the disclosed method and system as it is not necessary to measure the reflected light.

Furthermore, the disclosed method and system do not require the use of additional components such as a lock-in amplifier, a light detector such as a photodiode detector, a frequency modulator (a light chopper) and a light polarizer(s). Advantageously, the disclosed method and system may not require the need to measure reflected light from the fluid sample. Accordingly, the disclosed method and system may not require the use of a photodiode detector to detect the reflected light. Therefore, the disclosed method and system is less complicated than conventional techniques, more cost effective and is substantially easier for an end-user to operate.

Moreover, due to the need for a smaller number of components, introduction of error into the measurement system as a result of additional components that are normally present in conventional techniques is substantially minimized. Accordingly, the results obtained from the disclosed method and system may be more accurate than conventional techniques.

It will be apparent that various other modifications and adaptations of the invention will be apparent to the person skilled in the art after reading the foregoing disclosure without departing from the spirit and scope of the invention and it is intended that all such modifications, and adaptations come within the scope of the appended claims.

The invention claimed is:

1. A method for detecting surface plasmon resonance associated with a fluid sample, the method comprising the steps of:
providing a piezoelectric substrate having at least two electrodes thereon, wherein at least one of said electrodes is coupled to a fluid sample;
transmitting a light beam at a plurality of incident angles towards the piezoelectric substrate to induce an oscillation frequency detune in the piezoelectric substrate; and
measuring the oscillation frequency detune from said electrodes at each of said incident angles during transmittance of said light to detect surface plasmon resonance associated with the fluid sample.

2. A method according to claim 1, further comprising the step of using said measured oscillation frequency detune to determine a gravimetric parameter of said fluid sample.

3. A method according to claim 2, wherein said gravimetric parameter is a quartz crystal microbalance parameter.

4. A method according to claim 1, wherein a plurality of grating formations are provided on the surface of the piezoelectric substrate.

5. A method according to claim 4, wherein said grating formations have a grating constant of 300 nm to 750 nm.

6. A method according to claim 1, wherein said light beam is a laser light beam.

7. A method according to claim 6, wherein the intensity of said laser is selected from the range of 0.01 mW/mm$^2$ to 100 mW/mm$^2$.

8. A method according to claim 6, wherein the wavelength of said laser light is selected from the range of 500 nm to 1200 nm.

9. A method according to claim 1, further comprising the step of applying an electric field to said electrodes to thereby generate said oscillation frequency.

10. A system for detecting surface plasmon resonance associated with a fluid sample, the system comprising:
a piezoelectric substrate having at least two electrodes disposed thereon;
an enclosed chamber for retaining a fluid sample therein, wherein said enclosed chamber is arranged such that at least one of the electrodes is coupled to said fluid sample in use;
a light beam source that transmit a light beam at a plurality of incident angles towards said piezoelectric substrate to induce an oscillation frequency detune on said piezoelectric substrate; and
a means for measuring the oscillation frequency detune from said electrodes at each of said incident angles during transmittance of said light to detect surface plasmon resonance associated with said fluid sample.

11. A system according to claim 10, wherein the oscillation frequency detune is used to determine a gravimetric parameter of said sample.

12. A system according to claim 11, wherein said gravimetric parameter is a quartz crystal microbalance parameter.

13. A system according to claim 10, comprising means for moving said light beam and said fluid sample relative to each other.

14. A system according to claim 13, wherein the means for movement is coupled to at least one light reflective material to thereby reflect said transmitted light at a plurality of incident angles onto said fluid sample when said reflective material is moved.

15. A system according to claim 13, wherein the means for movement comprises a motor for moving at least one of the light beam source and the piezoelectric substrate.

16. A system according to claim 10, comprising an electric field generator for applying an electric field to said electrodes.

17. A system according to claim 10, wherein said enclosed chamber has an inlet conduit and an outlet conduit for transmittance of said sample therethrough.

18. A system according to claim 10, wherein said piezoelectric substrate has a plurality of grating formations disposed on the surface thereon that have at least one of the following: (i) a grating constant of from 300 nm to 750 nm; and (ii) grating heights of from 10 nm to 100 nm, and wherein said electrodes have thickness of from 20 nm to 2000 nm.

19. A system according to claim 10, wherein said light beam source is a source of laser light.

20. Use of a system comprising:

a piezoelectric substrate having at least two electrodes disposed thereon;

an enclosed chamber for retaining a fluid sample therein, wherein said enclosed chamber is arranged such that at least one of the electrodes is coupled to said fluid sample in use;

a light beam source that transmit a light beam at a plurality of incident angles towards said piezoelectric substrate to induce an oscillation frequency detune on said piezoelectric substrate; and means for measuring the oscillation frequency detune from said electrodes at each of said incident angles during transmittance of said light;

wherein said system is used to detect surface plasmon resonance associated with said fluid sample based on said measured oscillation frequency detune.

* * * * *